(12) United States Patent
Kaneko

(10) Patent No.: US 11,327,024 B2
(45) Date of Patent: May 10, 2022

(54) LEARNING MODEL PREPARATION METHOD, IMAGE PROCESSING METHOD, LEARNING MODEL PREPARATION DEVICE, AND COMPUTER-READABLE RECORDING MEDIUM

(71) Applicant: OLYMPUS CORPORATION, Tokyo (JP)

(72) Inventor: Yoshioki Kaneko, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 226 days.

(21) Appl. No.: 16/892,700

(22) Filed: Jun. 4, 2020

(65) Prior Publication Data

US 2020/0292460 A1  Sep. 17, 2020

Related U.S. Application Data

(63) Continuation of application No. PCT/JP2017/043842, filed on Dec. 6, 2017.

(51) Int. Cl.
| | | |
|---|---|---|
| *G01N 21/78* | (2006.01) | |
| *G01N 33/53* | (2006.01) | |
| *G06T 7/11* | (2017.01) | |

(52) U.S. Cl.
CPC ............. *G01N 21/78* (2013.01); *G01N 33/53* (2013.01); *G06T 7/11* (2017.01); *G06T 2207/20081* (2013.01)

(58) Field of Classification Search
CPC .... G11B 5/1871; G01N 21/251; G01N 21/78; G01N 33/53; G06T 2207/10024; G06T 2207/20081; G06T 7/11
See application file for complete search history.

(56) References Cited

U.S. PATENT DOCUMENTS

| | | |
|---|---|---|
| 4,687,736 A | 8/1987 | Newman et al. |
| 5,432,056 A | 7/1995 | Hartman et al. |
| 5,639,630 A | 6/1997 | Malin et al. |
| 5,643,722 A | 7/1997 | Rothschild et al. |
| 5,866,350 A | 2/1999 | Canavaggio et al. |

(Continued)

FOREIGN PATENT DOCUMENTS

| | | |
|---|---|---|
| JP | S62-502285 | 9/1987 |
| JP | H07-280808 A | 10/1995 |

(Continued)

OTHER PUBLICATIONS

International Search Report dated Feb. 13, 2018 issued in PCT/JP2017/043842.

*Primary Examiner* — Bobbak Safaipour

(74) *Attorney, Agent, or Firm* — Scully, Scott, Murphy & Presser, P.C.

(57) ABSTRACT

A learning model preparation method includes: acquiring a non-specific binding specimen image representing a non-specific binding specimen that allows a reagent to act on a tissue containing the endogenous protein, the reagent developing a color in a non-specific binding region in which an endogenous protein exists; and preparing a first learning model by setting the non-specific binding specimen image to first learning data, and by allowing a learning device to learn the non-specific binding region, based on the first learning data.

17 Claims, 16 Drawing Sheets

(56) References Cited

U.S. PATENT DOCUMENTS

| | | | |
|---|---|---|---|
| 9,002,077 B2* | 4/2015 | Hoyt | G06V 20/698 |
| | | | 382/128 |
| 2006/0154234 A1 | 7/2006 | Winther et al. | |
| 2008/0254492 A1 | 10/2008 | Tsuchiya | |
| 2009/0305307 A1 | 12/2009 | Sherwood | |
| 2018/0128834 A1* | 5/2018 | Jolley | G01N 33/6869 |

FOREIGN PATENT DOCUMENTS

| | | |
|---|---|---|
| JP | H08-308593 A | 11/1996 |
| JP | 2007-127505 A | 5/2007 |
| JP | 2007-527991 A | 10/2007 |
| JP | 2008-051821 A | 3/2008 |
| JP | 2008-275592 A | 11/2008 |
| JP | 2015-038467 A | 2/2015 |
| WO | WO 1986/005591 A1 | 9/1986 |
| WO | WO 2005/003773 A1 | 1/2005 |

* cited by examiner

WAVELENGTH [nm]

WAVELENGTH [nm]

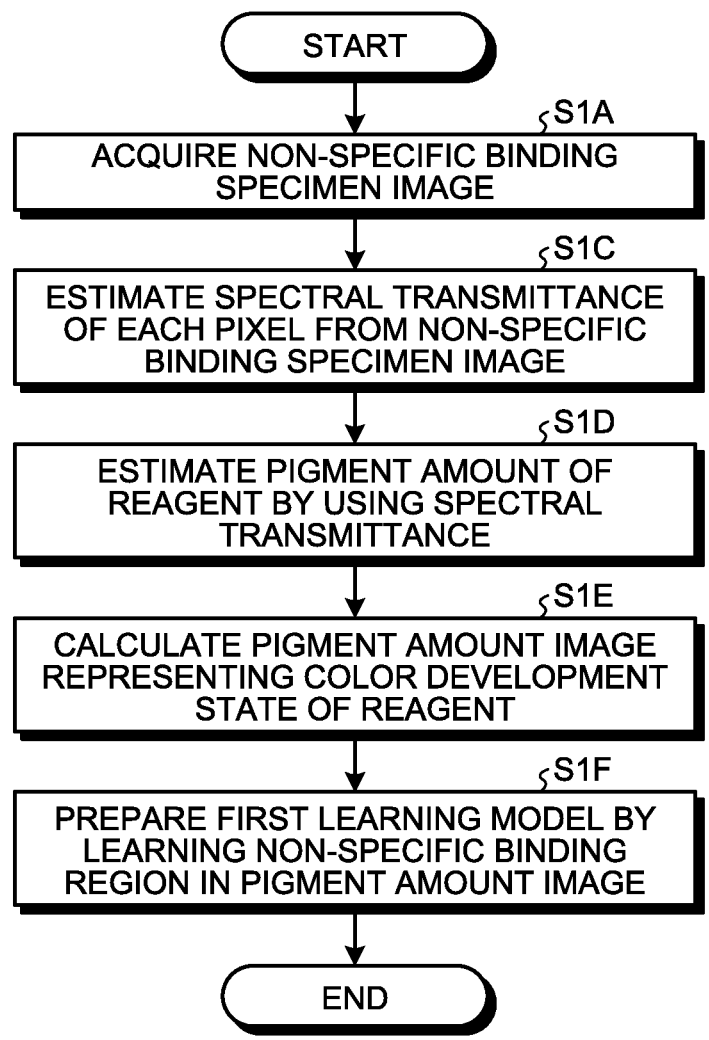

LEARNING MODEL PREPARATION METHOD, IMAGE PROCESSING METHOD, LEARNING MODEL PREPARATION DEVICE, AND COMPUTER-READABLE RECORDING MEDIUM

CROSS-REFERENCE TO RELATED APPLICATION

This application is a continuation of International Application No. PCT/JP2017/043842, filed on Dec. 6, 2017, the entire contents of which are incorporated herein by reference.

BACKGROUND

1. Technical Field

The present disclosure relates to a learning model preparation method, an image processing method, a learning model preparation device, an image processing device, and a computer-readable recording medium that are used for determining whether a pathological specimen is positive or negative.

2. Related Art

A pathological specimen of a patient that is an object to be inspected is prepared by extracting a specimen from the patient, and by performing a cutting step, a fixing step, an embedding step, a slicing step, a staining step, and a sealing step with respect to the extracted specimen.

Then, in the related art, a technology is proposed in which whether the pathological specimen is positive or negative is determined on the basis of a pathological specimen image obtained by imaging the pathological specimen (for example, refer to JP 2015-38467 A).

SUMMARY

In some embodiments, a learning model preparation method includes: acquiring a non-specific binding specimen image representing a non-specific binding specimen that allows a reagent to act on a tissue containing the endogenous protein, the reagent developing a color in a non-specific binding region in which an endogenous protein exists; and preparing a first learning model by setting the non-specific binding specimen image to first learning data, and by allowing a learning device to learn the non-specific binding region, based on the first learning data.

In some embodiments, an image processing method includes: acquiring a pathological specimen image representing a pathological specimen that is an object to be inspected; extracting the non-specific binding region in the pathological specimen image by using the first learning data that is prepared by the learning model preparation method; and displaying the non-specific binding region in the pathological specimen image on a display to be identifiable from other regions in the pathological specimen image.

In some embodiments, an image processing method includes: acquiring a pathological specimen image representing a pathological specimen that is an object to be inspected; extracting the non-specific binding region in the pathological specimen image by using the first learning model that is prepared by the learning model preparation method; excluding the non-specific binding region from the pathological specimen image; and determining whether the pathological specimen is positive or negative, based on the pathological specimen image excluding the non-specific binding region.

In some embodiments, an image processing method includes: acquiring a pathological specimen image representing a pathological specimen that is an object to be inspected; and determining whether the pathological specimen is positive or negative from the pathological specimen image by using the second learning model that is prepared by the learning model preparation method.

In some embodiments, a learning model preparation device includes: a first image acquisition circuit configured to acquire a non-specific binding specimen image representing a non-specific binding specimen that allows a reagent to act on a tissue containing the endogenous protein, the reagent developing a color in a non-specific binding region in which an endogenous protein exists; and a first learning model preparation circuit configured to prepare a first learning model by setting the non-specific binding specimen image to first learning data, and by learning the non-specific binding region.

In some embodiments, an image processing device includes: a third image acquisition circuit configured to acquire a pathological specimen image representing a pathological specimen that is an object to be inspected; an extraction circuit configured to extract the non-specific binding region in the pathological specimen image by using the first learning data that is prepared by the learning model preparation device; and a display controller configured to display the non-specific binding region in the pathological specimen image on a display to be identifiable from other regions in the pathological specimen image.

In some embodiments, an image processing device includes: a third image acquisition circuit configured to acquire a pathological specimen image representing a pathological specimen that is an object to be inspected; an extraction circuit configured to extract the non-specific binding region in the pathological specimen image by using the first learning model that is prepared by the learning model preparation device; a masking process circuit configured to exclude the non-specific binding region from the pathological specimen image; and a determination circuit configured to determine whether the pathological specimen is positive or negative, based on the pathological specimen image excluding the non-specific binding region.

In some embodiments, an image processing device includes: a third image acquisition circuit configured to acquire a pathological specimen image representing a pathological specimen that is an object to be inspected; and a determination circuit configured to determine whether the pathological specimen is positive or negative from the pathological specimen image by using the second learning model that is prepared by the learning model preparation device.

In some embodiments, provided is a non-transitory computer-readable recording medium with an executable program stored thereon. The program is a learning model preparation program allowing a computer to execute the learning model preparation method.

In some embodiments, provided is a non-transitory computer-readable recording medium with an executable program stored thereon. The program is an image processing program allowing a computer to execute the image processing method.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 22 is a flowchart illustrating a learning model preparation method according to the sixth embodiment.

DETAILED DESCRIPTION

Figure 1:
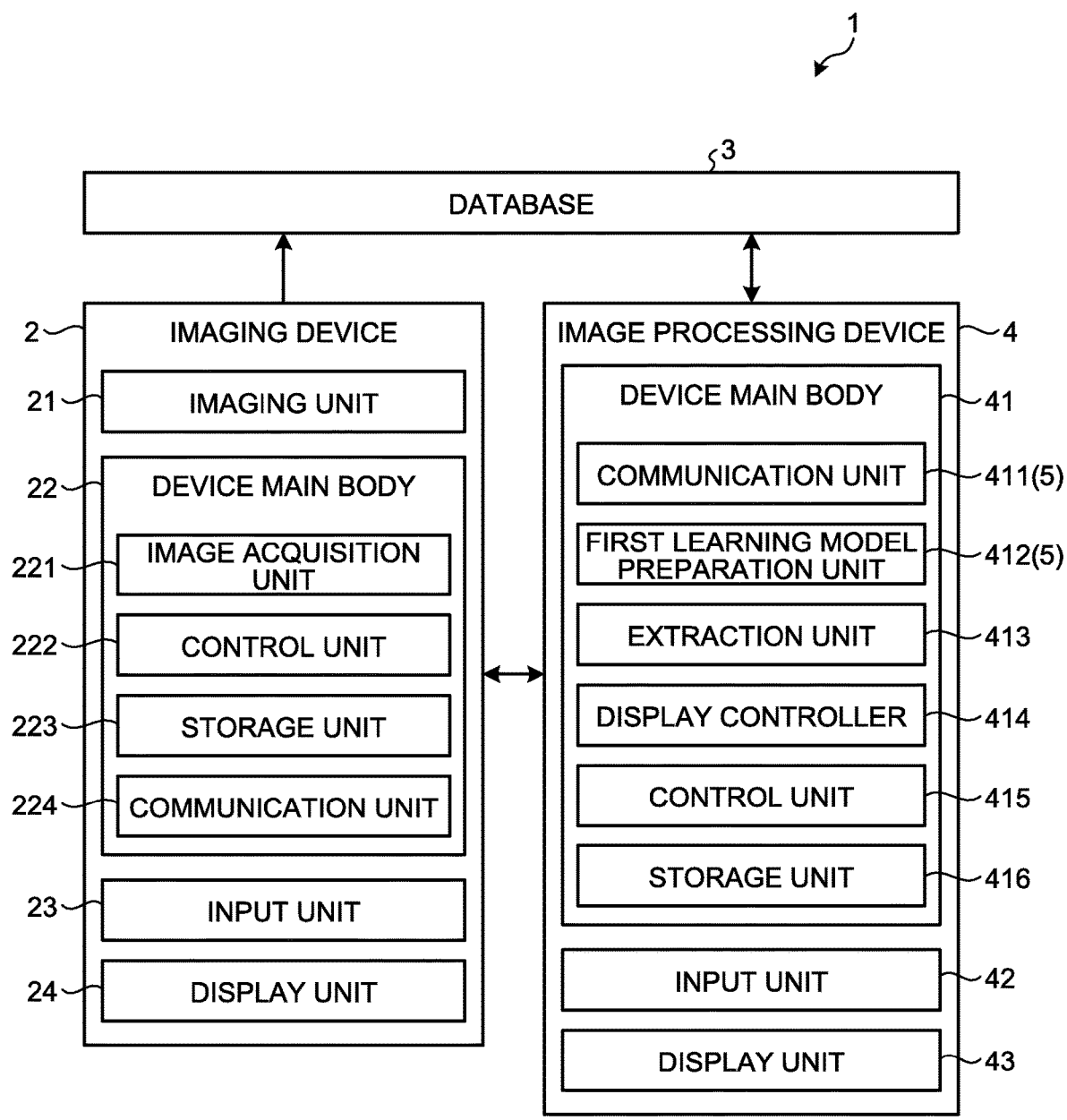
FIG. 1 is a block diagram illustrating an image processing system according to a first embodiment.

Hereinafter, modes for implementing the disclosure (hereinafter, embodiments) will be described with reference to the drawings. Note that, the disclosure is not limited to the following embodiments. Further, in the description of the drawings, the same reference numerals will be applied to the same parts.

First Embodiment

Overall Configuration of Image Processing System

FIG. 1 is a block diagram illustrating an image processing system 1 according to a first embodiment.

The image processing system 1 is a system in which a pathological specimen of an object to be inspected that is stained is imaged, and a pathological specimen image obtained by the imaging is processed. As illustrated in FIG. 1, the image processing system 1 includes an imaging device 2, a database 3, and an image processing device 4.

Even though it is not specifically illustrated, the imaging device 2, the database 3, and the image processing device 4 are connected to each other through a network such that communication can be performed with each other. The internet, a local area network (LAN), a virtual private network (VPN), or the like can be exemplified as the network, regardless of whether the network is wired or wireless.

Figure 2A:
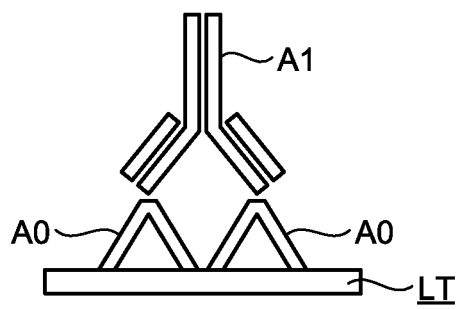
FIG. 2A is a diagram describing a preparation method of a pathological specimen.
Figure 2B:
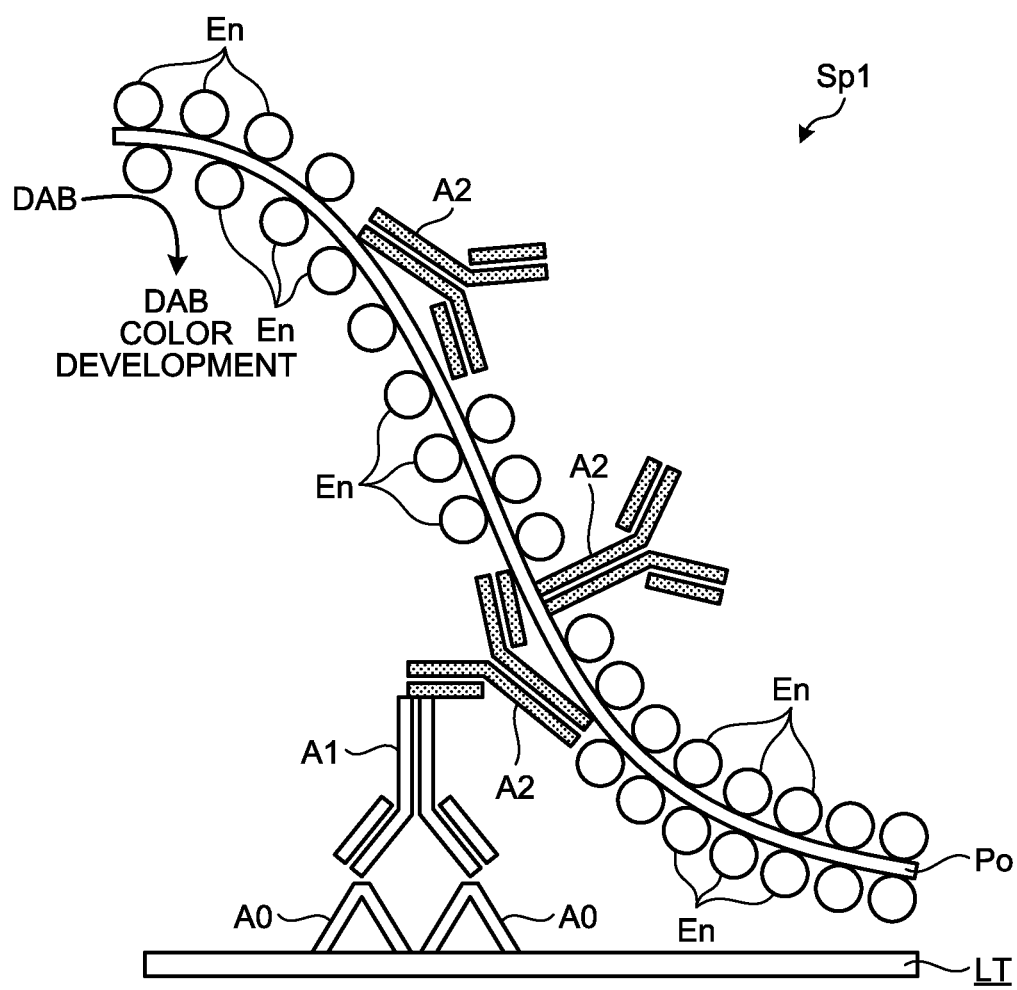
FIG. 2B is a diagram describing the preparation method of the pathological specimen.

FIG. 2A and FIG. 2B are diagrams describing a preparation method of a pathological specimen Sp1.

Here, in the first embodiment, the pathological specimen Sp1 is stained by a staining method illustrated in FIG. 2A and FIG. 2B. Note that, the staining method illustrated in FIG. 2A and FIG. 2B is a polymer method that is one of staining methods for immunostaining.

Specifically, as illustrated in FIG. 2A, an operator allows a primary antibody A1 to act on a tissue LT, and binds the primary antibody A1 to an antigen A0 in the tissue LT. After that, the operator cleans the tissue LT. As a result thereof, the primary antibody A1 that is not bound to the antigen A0 is removed from the tissue LT.

Next, as illustrated in FIG. 2B, the operator allows a dextran polymer Po in which a secondary antibody A2 and a large amount of enzyme En are bound to act on the tissue LT, and binds the secondary antibody A2 (the dextran polymer Po) to the primary antibody A1. Here, in the first embodiment, peroxidase (for example, horseradish peroxidase (HRP)) is adopted as the enzyme En. After that, the operator cleans the tissue LT. As a result thereof, the secondary antibody A2 (the dextran polymer Po) that is not bound to the primary antibody A1 is removed from the tissue LT.

Finally, the operator allows diaminobenzidine (3,3-diaminobenzidine: DAB) to act on the tissue LT. As a result thereof, the enzyme En that is bound to the dextran polymer Po reacts with the DAB, and thus, the DAB develops a color.

According to the processes described above, a pathological specimen Sp1 is prepared in which it is possible to check the position of the antigen A0 in accordance with a color development position of the DAB.

Configuration of Imaging Device

The imaging device 2 is a device that acquires a specimen image of a specimen Sp (refer to FIG. 3) such as the pathological specimen Sp1 described above. Here, in the first embodiment, the imaging device 2 is configured as a device that acquires a specimen image of a multiband image. As illustrated in FIG. 1, the imaging device 2 includes an imaging unit 21, a device main body 22, an input unit 23, and a display unit 24.

Figure 3:
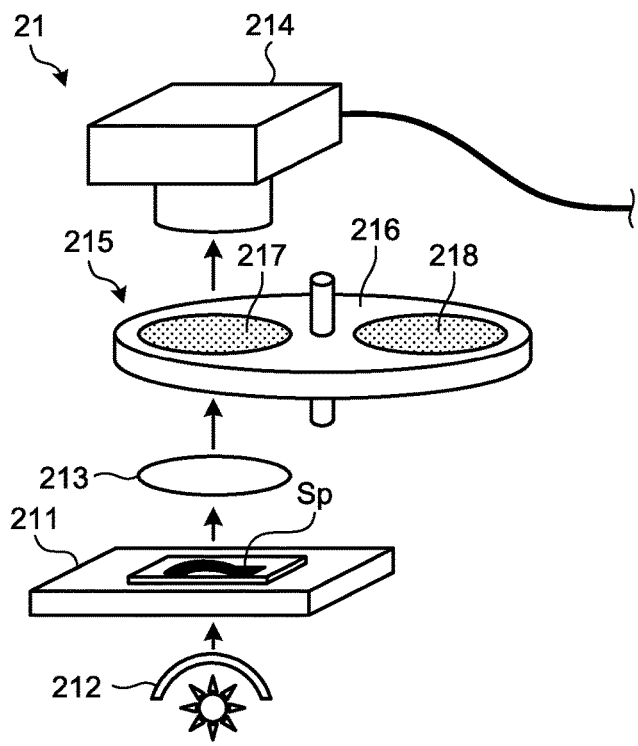
FIG. 3 is a diagram schematically illustrating a configuration of an imaging unit.

FIG. 3 is a diagram schematically illustrating the configuration of the imaging unit 21.

The imaging unit 21 is a part in which the specimen image is acquired, and as illustrated in FIG. 3, includes a stage 211, an illumination unit 212, an imaging optical system 213, an RGB camera 214, and a filter part 215.

The stage 211 is a part on which the specimen Sp is mounted, and is capable of changing an observation site of the specimen Sp by being moved under the control of the device main body 22.

The illumination unit 212 irradiates the specimen Sp mounted on the stage 211 with illumination light, under the control of the device main body 22.

The imaging optical system 213 images transmitted light that is emitted to the specimen Sp and is transmitted through the specimen Sp, with the RGB camera 214.

Figure 4:
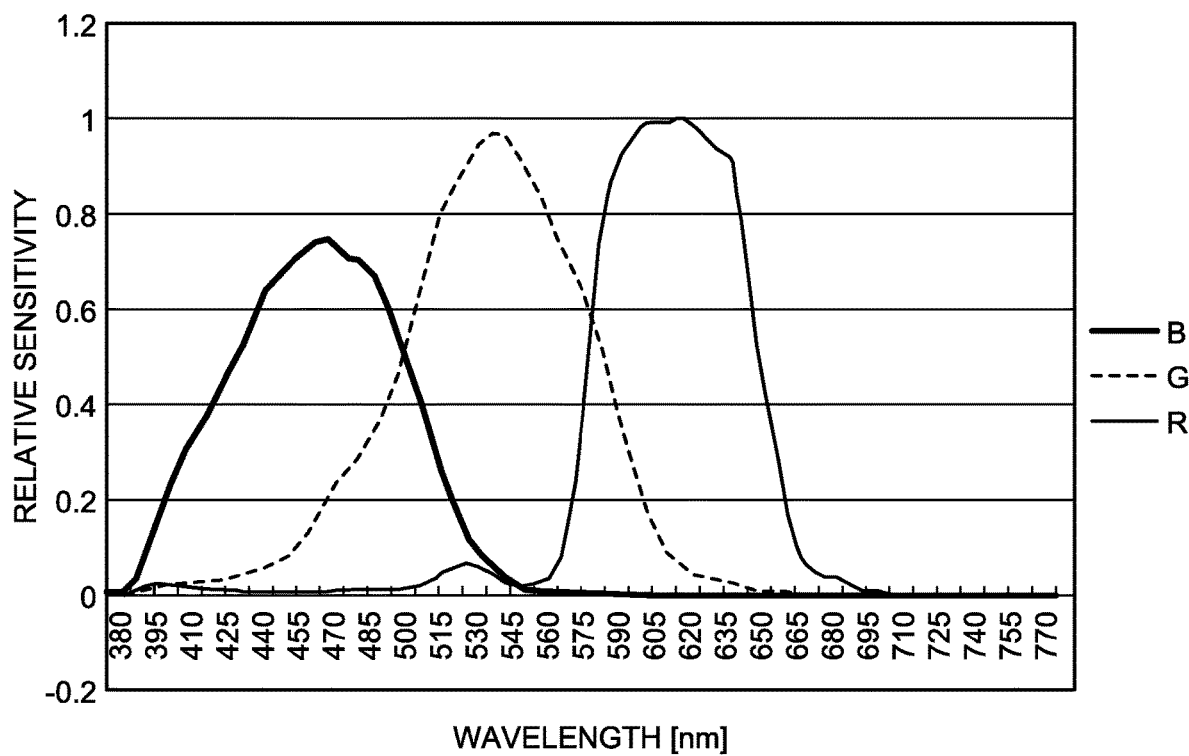
FIG. 4 is a diagram illustrating an example of spectral sensitivity properties of an RGB camera.

FIG. 4 is a diagram illustrating an example of spectral sensitivity properties of the RGB camera 214.

The RGB camera 214 includes an image sensor such as charge coupled device (CCD) or a complementary metal oxide semiconductor (CMOS), and images the transmitted light that is transmitted through the specimen Sp, under the control of the device main body 22. The RGB camera 214, for example, has spectral sensitivity properties of each band of red (R), green (G), and blue (B) illustrated in FIG. 4.

Figure 5:
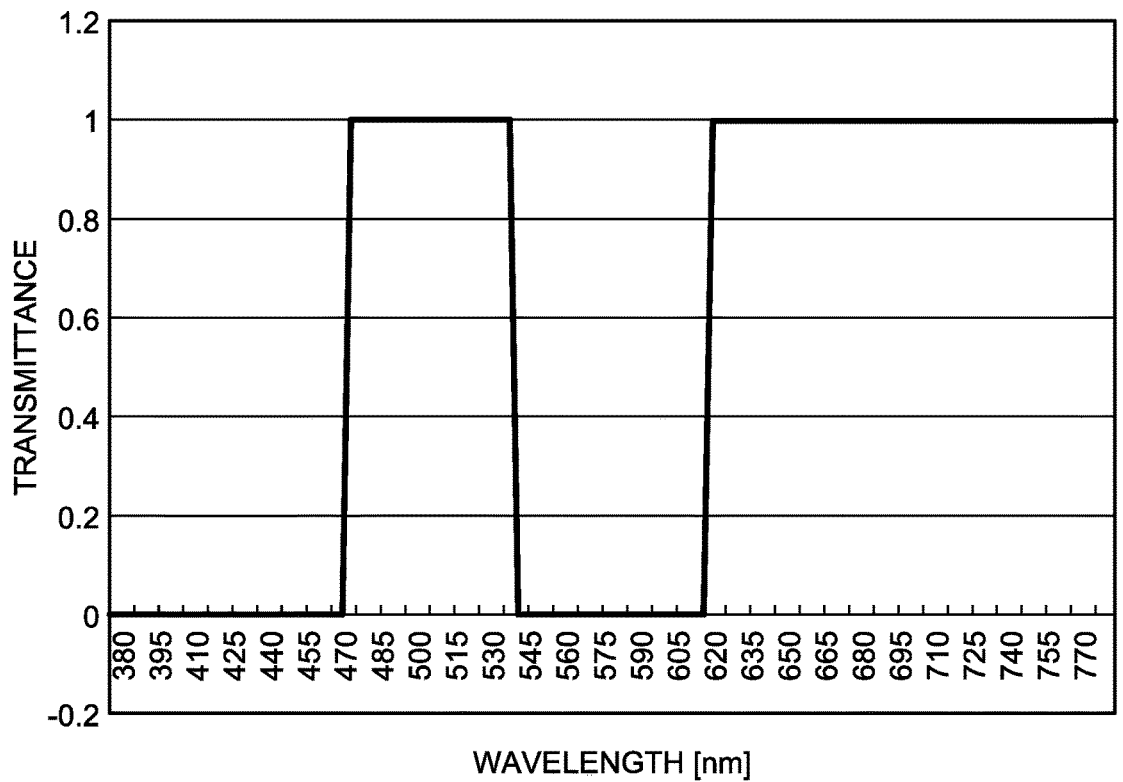
FIG. 5 is a diagram illustrating an example of spectral properties of a first filter.
Figure 6:
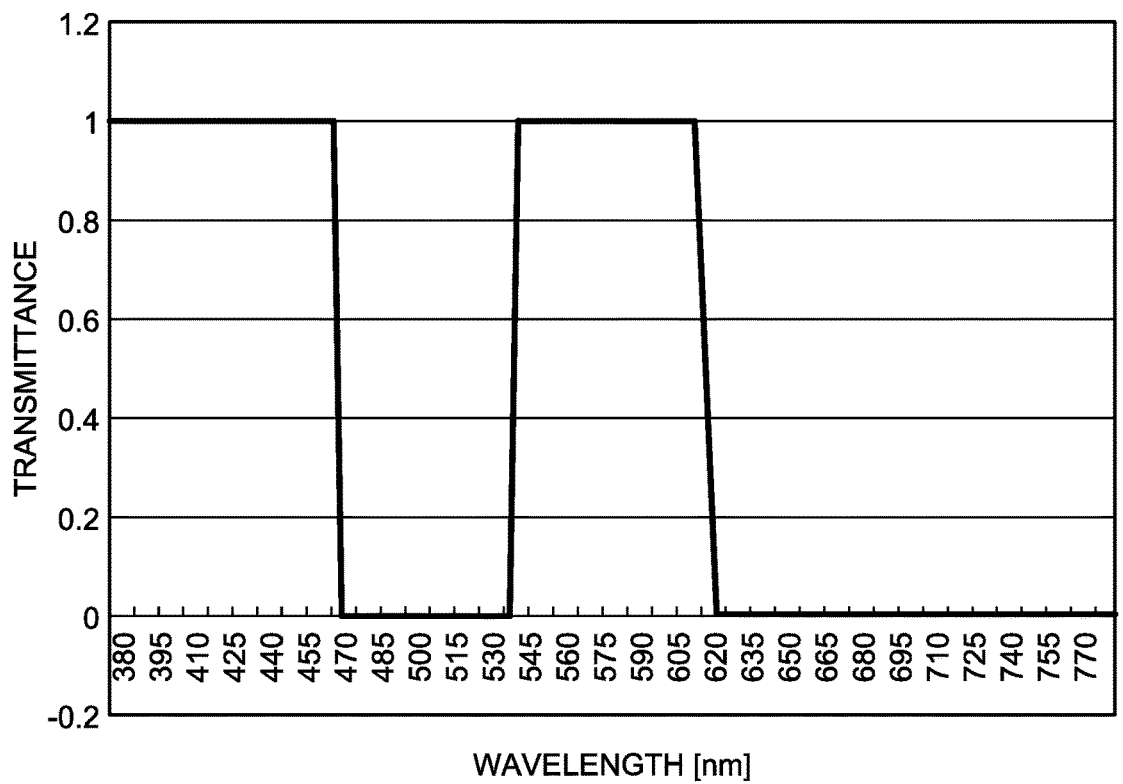
FIG. 6 is a diagram illustrating an example of spectral properties of a second filter.

FIG. 5 is a diagram illustrating an example of spectral properties of a first filter 217. FIG. 6 is a diagram illustrating an example of spectral properties of a second filter 218.

The filter part 215 is arranged on an optical path from the imaging optical system 213 to the RGB camera 214, and limits a wavelength band of light to be imaged by the RGB camera 214 to a predetermined range. As illustrated in FIG. 3, the filter part 215 includes a filter wheel 216 that can be rotated under the control of the device main body 22, and the first filter 217 and the second filter 218 that are provided in the filter wheel 216 and have spectral properties different from each other (for example, the spectral properties of FIG. 5 and FIG. 6) such that a transmission wavelength band of each band of R, G, and B is halved.

Then, the imaging unit 21 acquires the specimen image (the multiband image) of the specimen Sp, under the control of the device main body 22, as follows.

First, the imaging unit 21 performs positioning with respect to the first filter 217 on the optical path from the illumination unit 212 to the RGB camera 214, and irradiates the specimen Sp with the illumination light from the illumination unit 212. Then, the RGB camera 214 images the transmitted light that is transmitted through the specimen Sp, the first filter 217, and the imaging optical system 213 (first imaging).

Next, the imaging unit 21 performs positioning with respect to the second filter 218 on the optical path from the illumination unit 212 to the RGB camera 214, and performs second imaging as with the first imaging.

Accordingly, images of three bands different from each other are acquired in the first imaging and the second imaging, and specimen images of a total of six bands are acquired.

Note that, the number of filters provided in the filter part 215 is not limited to 2, three or more filters may be provided, and thus, images of more bands may be acquired. In addition, the imaging unit 21 may be configured such that the filter part 215 is omitted, and only RGB images are acquired by the RGB camera 214. Further, a liquid crystal tunable filter or an acousto-optical tunable filter that is capable of changing the spectral properties may be adopted instead of the filter part 215. In addition, the specimen image (the multiband image) may be acquired by switching a plurality of light rays having different spectral properties, and by irradiating the specimen Sp with the light. Further, a black and white camera may be adopted instead of the RGB camera 214.

The device main body 22, for example, includes a personal computer (PC) or the like, and integrally controls the operation of the imaging unit 21. As illustrated in FIG. 1, the device main body 22 includes an image acquisition unit 221, a control unit 222, a storage unit 223, and a communication unit 224.

The image acquisition unit 221 includes an interface that imports the specimen image (image data) output from the imaging unit 21.

The control unit 222 includes a central processing unit (CPU) or the like. The control unit 222 acquires the specimen image by controlling the operation of the image acquisition unit 221 or the imaging unit 21, on the basis of an input signal input from the input unit 23, a program or data stored in the storage unit 223, and the like. In addition, the control unit 222 outputs a display signal to the display unit 24, and allows the display unit 24 to display various screens.

The storage unit 223 includes various IC memories such as a read only memory (ROM) such as a flash memory that is capable of performing update recording and a random access memory (RAM), a hard disk that is built in or is connected by a data communication terminal, an information storage device such as a CD-ROM, a writing/reading device that writes/reads information with respect to the information storage device, and the like, and stores a program that is executed by the control unit 222, the specimen image that is acquired by the image acquisition unit 221, and the like.

The communication unit 224 is an interface that performs communication control with respect to the database 3 or the image processing device 4.

The input unit 23, for example, includes various input devices such as a keyboard or a mouse, a touch panel, and various switches, and receives an input manipulation of a user. Then, the input unit 23 outputs a signal according to the input manipulation to the control unit 222.

The display unit 24 is attained by a display device such as a liquid crystal display (LCD), an electroluminescence (EL) display, and a cathode ray tube (CRT) display, and displays various screens, on the basis of the display signal that is input from the control unit 222.

Configuration of Database

The database 3, for example, is provided in a known server device in a hospital or a specimen preparation company, or on a cloud, and records a plurality of non-specific binding specimen images described below.

Figure 7:
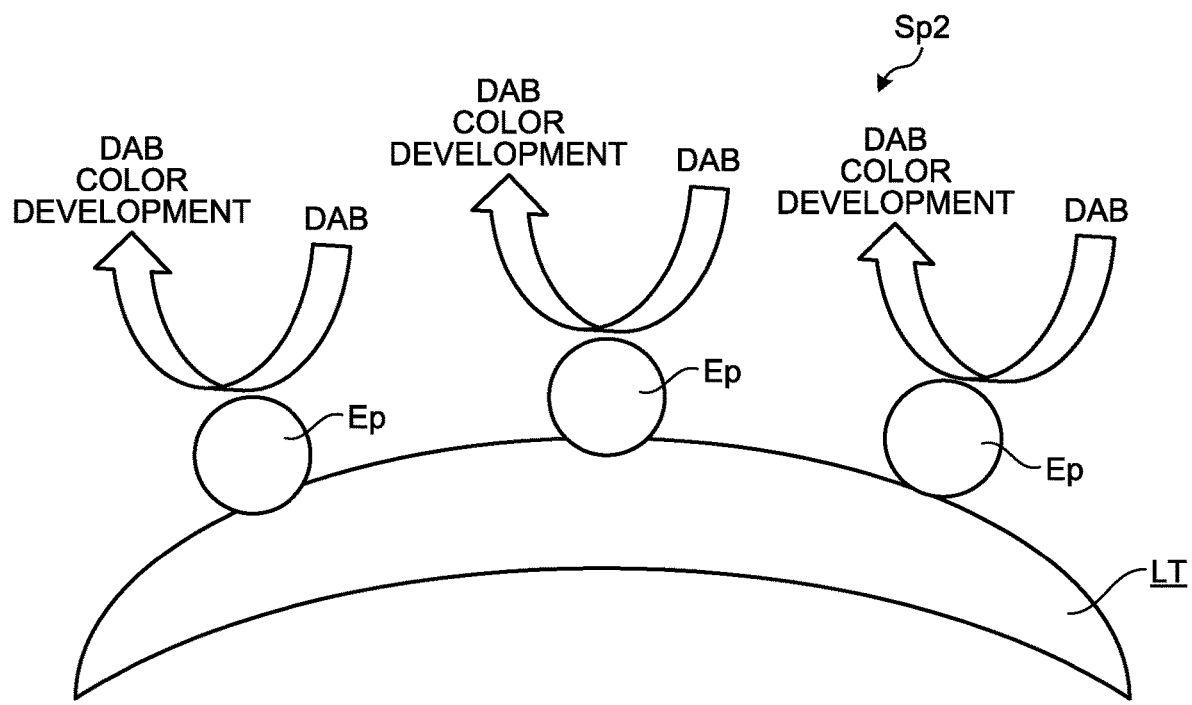
FIG. 7 is a diagram describing a preparation method of a non-specific binding specimen.

FIG. 7 is a diagram describing a preparation method of a non-specific binding specimen Sp2.

The non-specific binding specimen image is a specimen image of the non-specific binding specimen Sp2 that is prepared by the preparation method of FIG. 7, and is a specimen image that is acquired by the imaging device 2.

However, there are many tissues LT containing endogenous peroxidase as an endogenous protein. For this reason, in the pathological specimen Sp1, a non-specific binding region may be generated in which the DAB reacts with the endogenous peroxidase and develops the color. That is, in the pathological specimen Sp1, it is difficult to discriminate whether it is the position of the antigen A0 or the position of the non-specific binding region (a position in which the endogenous protein (the endogenous peroxidase) exists) from the color development position of the DAB. Therefore, the non-specific binding specimen Sp2 is used in order to separate the position of the antigen A0 from the position of the non-specific binding region.

Specifically, as illustrated in FIG. 7, the operator allows the DAB to directly act on the tissue LT. Accordingly, the non-specific binding specimen Sp2 that allows the DAB to develop the color by the endogenous peroxidase only in the non-specific binding region in which the endogenous peroxidase that is an endogenous protein Ep exists is prepared.

Configuration of Image Processing Device

The image processing device 4 acquires a pathological specimen image of the pathological specimen Sp1 from the imaging device 2, and processes the pathological specimen image. As illustrated in FIG. 1, the image processing device 4 includes a device main body 41, an input unit 42, and a display unit 43.

The device main body 41, for example, includes a personal computer (PC) or the like. As illustrated in FIG. 1, the device main body 41 includes a communication unit 411, a first learning model preparation unit 412, an extraction unit 413, a display controller 414, a control unit 415, and a storage unit 416.

The communication unit 411 is an interface that performs communication control with respect to the database 3 or the imaging device 2, and has a function as a first image acquisition unit and a third image acquisition unit according to the disclosure.

The first learning model preparation unit 412 prepares a first learning model by setting the plurality of non-specific binding specimen images acquired from the database 3 through the communication unit 411 to first learning data, and by learning the non-specific binding region, on the basis of the first learning data. Here, mechanical learning such as linear discrimination or structured learning can be exemplified as the learning. Then, the first learning model preparation unit 412 stores the first learning model in the storage unit 416.

The communication unit 411 and the first learning model preparation unit 412 described above configure a learning model preparation device 5 according to the disclosure (FIG. 1).

The extraction unit 413 extracts the non-specific binding region in the pathological specimen image that is acquired from the imaging device 2 through the communication unit 411 by using the first learning model stored in the storage unit 416.

The display controller 414 allows the display unit 43 to display the non-specific binding region that is extracted by the extraction unit 413 to be identifiable from other regions in the pathological specimen image.

The control unit 415 includes a CPU or the like, and controls the overall operation of the image processing device 4, on the basis of an input signal input from the input unit 42, a program or data stored in the storage unit 416, and the like.

The storage unit 416 includes various IC memories such as a ROM such as a flash memory that is capable of performing update recording and a RAM, a hard disk that is built in or is connected by a data communication terminal, an information storage device such as a CD-ROM, a writing/reading device that writes/reads information with respect to the information storage device, and the like, and stores a program that is executed by the control unit 415 (including a learning model preparation program and an image processing program according to the disclosure), the first learning model that is prepared by the first learning model preparation unit 412, and the like.

The input unit 42, for example, includes various input devices such as a keyboard or a mouse, a touch panel, and various switches, and receives an input manipulation of the user. Then, the input unit 42 outputs a signal according to the input manipulation to the control unit 415.

The display unit 43 is attained by a display device such as an LCD, an EL display, and a CRT display, and displays various screens, on the basis of a display signal that is input from the control unit 415.

Operation of Image Processing Device Next, in the operation of the image processing device 4 described above, a learning model preparation method and an image processing method will be sequentially described.

Figure 8:
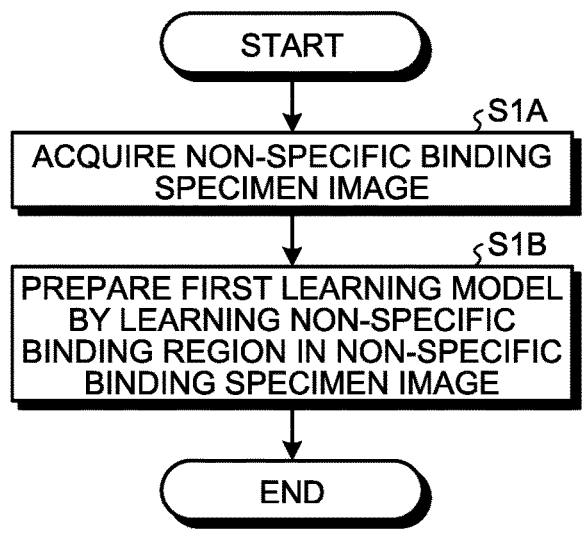
FIG. 8 is a flowchart illustrating a learning model preparation method.

FIG. 8 is a flowchart illustrating the learning model preparation method.

First, the communication unit 411 acquires the plurality of non-specific binding specimen images recorded in the database 3, under the control of the control unit 415 (Step S1A: a first image acquisition step).

After Step S1A, the first learning model preparation unit 412 prepares the first learning model by learning the non-specific binding region in the plurality of non-specific binding specimen images, under the control of the control unit 415 (Step S1B: a first learning model preparation step). Then, the first learning model preparation unit 412 stores the first learning model in the storage unit 416.

Figure 9:
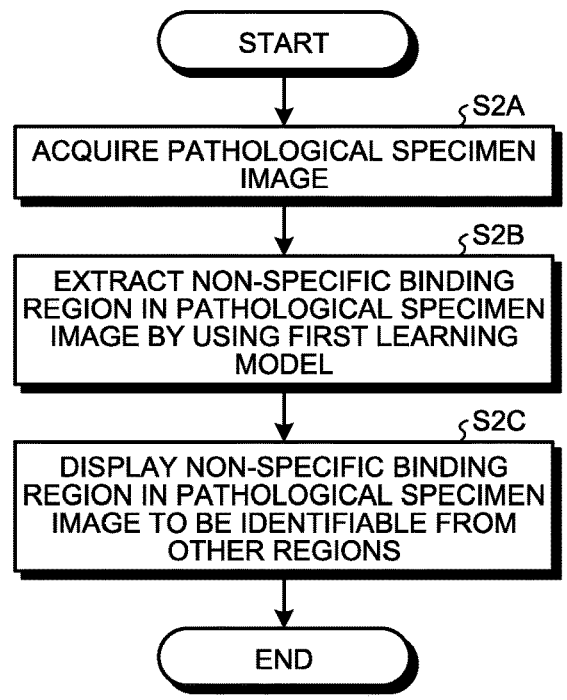
FIG. 9 is a flowchart illustrating an image processing method.

FIG. 9 is a flowchart illustrating the image processing method.

First, the communication unit 411 acquires the pathological specimen image from the imaging device 2, under the control of the control unit 415 (Step S2A: a third image acquisition step).

After Step S2A, the extraction unit 413 extracts the non-specific binding region in the pathological specimen image by using the first learning model stored in the storage unit 416, under the control of the control unit 415 (Step S2B: an extraction step).

After Step S2B, the display controller 414 allows the display unit 43 to display the non-specific binding region that is extracted in Step S2B to be identifiable from the other regions in the pathological specimen image, under the control of the control unit 415 (Step S2C: a display step).

Then, a medical doctor determines whether the pathological specimen Sp1 is positive or negative, while checking the pathological specimen image displayed on the display unit 43 (the non-specific binding region is displayed to be identifiable from the other regions).

According to the first embodiment described above, the following effects are obtained.

The image processing device 4 according to the first embodiment acquires the non-specific binding specimen image representing the non-specific binding specimen Sp2 that allows the reagent (DAB) developing the color in the non-specific binding region in which the endogenous protein Ep exists to act on the tissue LT containing the endogenous protein Ep. In addition, the image processing device 4 prepares the first learning model by setting the non-specific binding specimen image to the first learning data, and by learning the non-specific binding region, on the basis of the first learning data. Further, the image processing device 4 acquires the pathological specimen image representing the pathological specimen Sp1 that is the object to be inspected, and extracts the non-specific binding region in the pathological specimen image by using the first learning data. Then, the image processing device 4 allows the display unit 43 to display the non-specific binding region in the pathological specimen image to be identifiable from the other regions.

Therefore, the medical doctor is capable of setting only a part that is stained by specific binding (the position of the antigen A0) to a diagnostic target, while checking the pathological specimen image displayed on the display unit 43 (the non-specific binding region is displayed to be identifiable from the other regions). That is, the medical doctor is capable of accurately determining whether the pathological specimen Sp1 is positive or negative.

Modification Example 1-1 of First Embodiment

Figure 10:
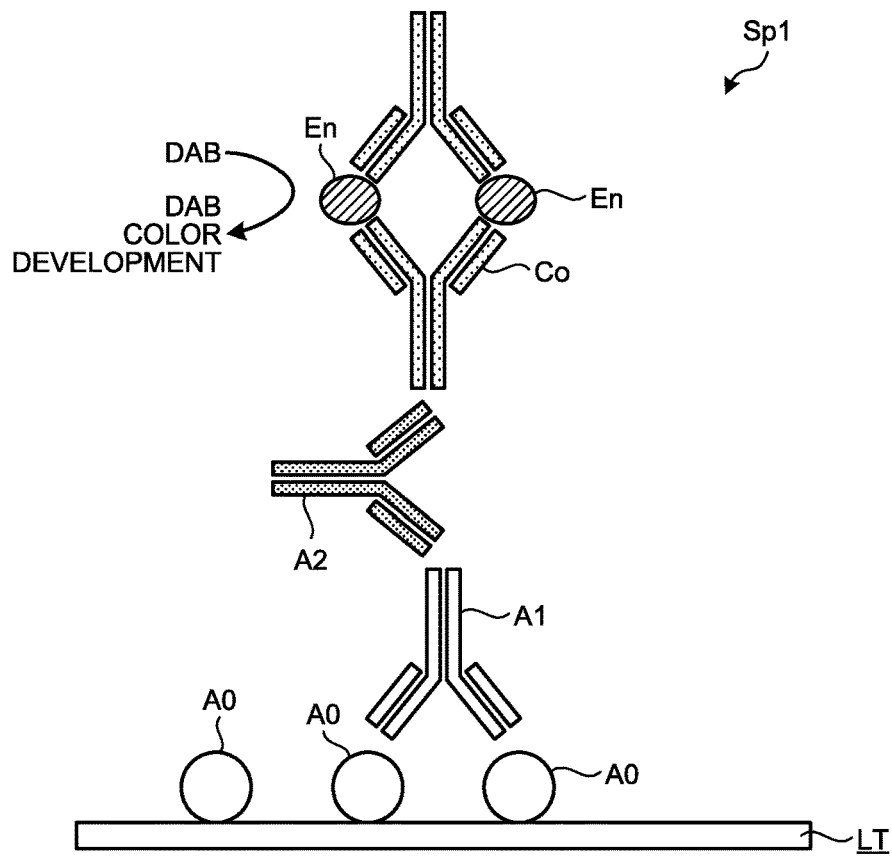
FIG. 10 is a diagram illustrating Modification Example 1-1 of the first embodiment.

FIG. 10 is a diagram illustrating Modification Example 1-1 of the first embodiment.

In the first embodiment described above, the polymer method (FIG. 2A and FIG. 2B) is adopted as a preparation method of the pathological specimen Sp1, but the preparation method is not limited thereto, and a PAP method illustrated in FIG. 10 may be adopted.

Specifically, the operator allows the primary antibody A1 to act on the tissue LT, and binds the primary antibody A1 to the antigen A0 in the tissue LT. After that, the operator cleans the tissue LT. As a result thereof, the primary antibody A1 that is not bound to the antigen A0 is removed from the tissue LT.

Next, the operator allows the secondary antibody A2 to act on the tissue LT, and binds the secondary antibody A2 to the primary antibody A1. After that, the operator cleans the tissue LT. As a result thereof, the secondary antibody A2 that is not bound to the primary antibody A1 is removed from the tissue LT.

Next, the operator allows a peroxidase antiperoxidase antibody complex Co to act on the tissue LT, and binds the peroxidase antiperoxidase antibody complex Co to the secondary antibody A2. After that, the operator cleans the tissue LT. As a result thereof, the peroxidase antiperoxidase antibody complex Co that is not bound to the secondary antibody A2 is removed from the tissue LT.

Finally, the operator allows the DAB to act on the tissue LT. As a result thereof, the enzyme (peroxidase) En contained in the peroxidase antiperoxidase antibody complex Co and the DAB react with each other, and thus, the DAB develops the color.

According to the processes described above, the pathological specimen Sp1 is prepared.

Note that, even in a case where the pathological specimen Sp1 is prepared by the PAP method, the same method as that in the first embodiment described above can be adopted as a preparation method of the non-specific binding specimen Sp2.

Modification Example 1-2 of First Embodiment

In the first embodiment and Modification Example 1-1 described above, when the pathological specimen Sp1 and the non-specific binding specimen Sp2 are prepared (FIG. 2A, FIG. 2B, FIG. 7, and FIG. 10), aminoethyl carbazole (3-amino-9-ethylcarbazole: AEC) or the like may be used instead of the DAB.

In addition, in the first embodiment and Modification Example 1-1 described above, the endogenous peroxidase is assumed as the endogenous protein Ep, but the endogenous protein Ep is not limited thereto, and endogenous alkali phosphatase may be assumed as the endogenous protein Ep. In this case, when the pathological specimen Sp1 is prepared (FIG. 2A, FIG. 2B, and FIG. 10), alkali phosphatase is used as the enzyme En, instead of the peroxidase. In addition, when the pathological specimen Sp1 and the non-specific binding specimen Sp2 are prepared (FIG. 2A, FIG. 2B, FIG. 7, and FIG. 10), fast red or new fuchsin, 5-bromo-4-chloro-3-Indoxyl phosphate/nitro blue tetrazolium chloride (BCIP/NBT), or the like is used instead of the DAB.

Second Embodiment

Next, a second embodiment will be described.

In the following description, the same reference numerals will be applied to the same configurations and the same steps as those in the first embodiment described above, and the detailed description thereof will be omitted or simplified.

In the second embodiment, only the preparation method of the pathological specimen Sp1 and the non-specific binding specimen Sp2 is different from that in the first embodiment described above.

Hereinafter, the preparation method of the pathological specimen Sp1 and the non-specific binding specimen Sp2 according to the second embodiment will be sequentially described.

Figure 11:
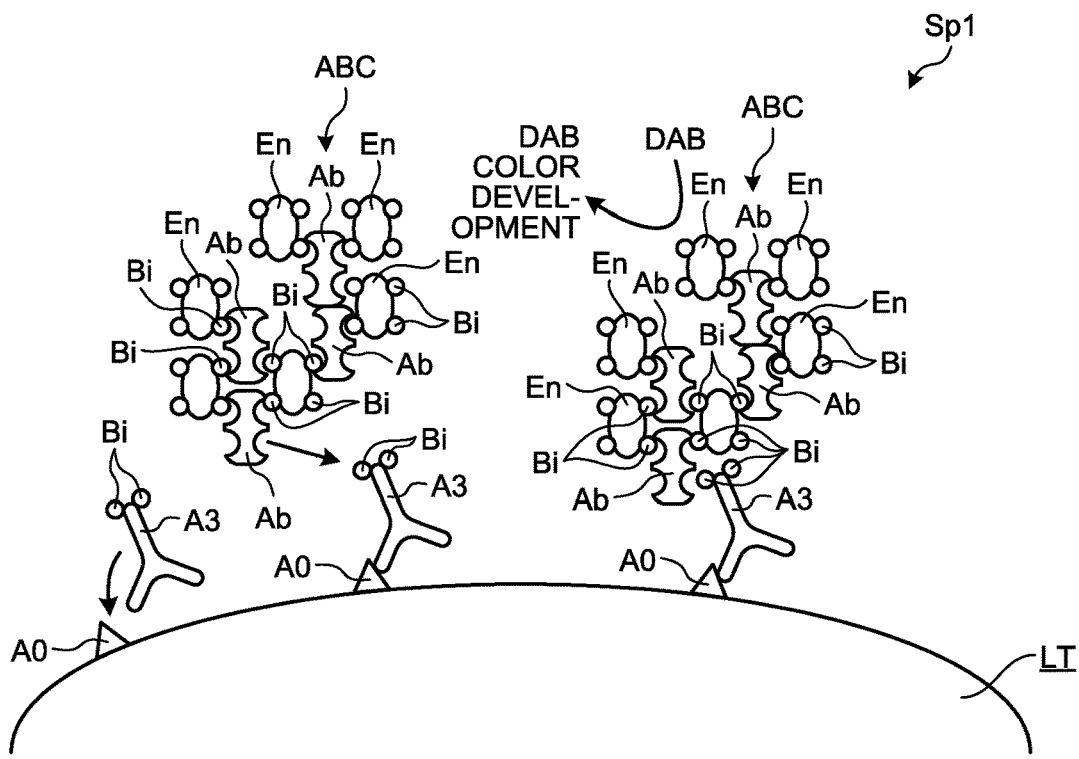
FIG. 11 is a diagram describing a preparation method of a pathological specimen according to a second embodiment.

Preparation Method of Pathological Specimen FIG. 11 is a diagram describing the preparation method of the pathological specimen Sp1 according to the second embodiment.

In the second embodiment, the pathological specimen Sp1 is stained by a staining method illustrated in FIG. 11. Note that, the staining method illustrated in FIG. 11 is an avidin-biotin complex (ABC) method that is one of the staining methods for immunostaining.

Specifically, as illustrated on the left side of FIG. 11, the operator allows a biotinylated antibody A3 to act on the tissue LT, and binds the biotinylated antibody A3 to the antigen A0 in the tissue LT. After that, the operator cleans the tissue LT. As a result thereof, the biotinylated antibody A3 that is not bound to the antigen A0 is removed from the tissue LT.

Next, as illustrated in the center of FIG. 11, the operator allows an avidin-biotin complex ABC in which avidin Ab having a plurality of reactive groups and the enzyme (the peroxidase) En biotinylated in a plurality of sites are mixed in advance at a suitable ratio to act on the tissue LT. Then, the avidin Ab contained in the avidin-biotin complex ABC is bound to the biotin Bi of the biotinylated antibody A3. After that, the operator cleans the tissue LT. As a result thereof, the avidin-biotin complex ABC (the avidin Ab) that is not bound to the biotinylated antibody A3 (the biotin Bi) is removed from the tissue LT.

Finally, the operator allows the DAB to act on the tissue LT. As a result thereof, as illustrated on the right side of FIG. 11, the enzyme (the peroxidase) En contained in the avidin-biotin complex ABC and the DAB react with each other, and thus, the DAB develops the color.

According to the processes described above, the pathological specimen Sp1 is prepared.

Preparation Method of Non-Specific Binding Specimen

Figure 12:
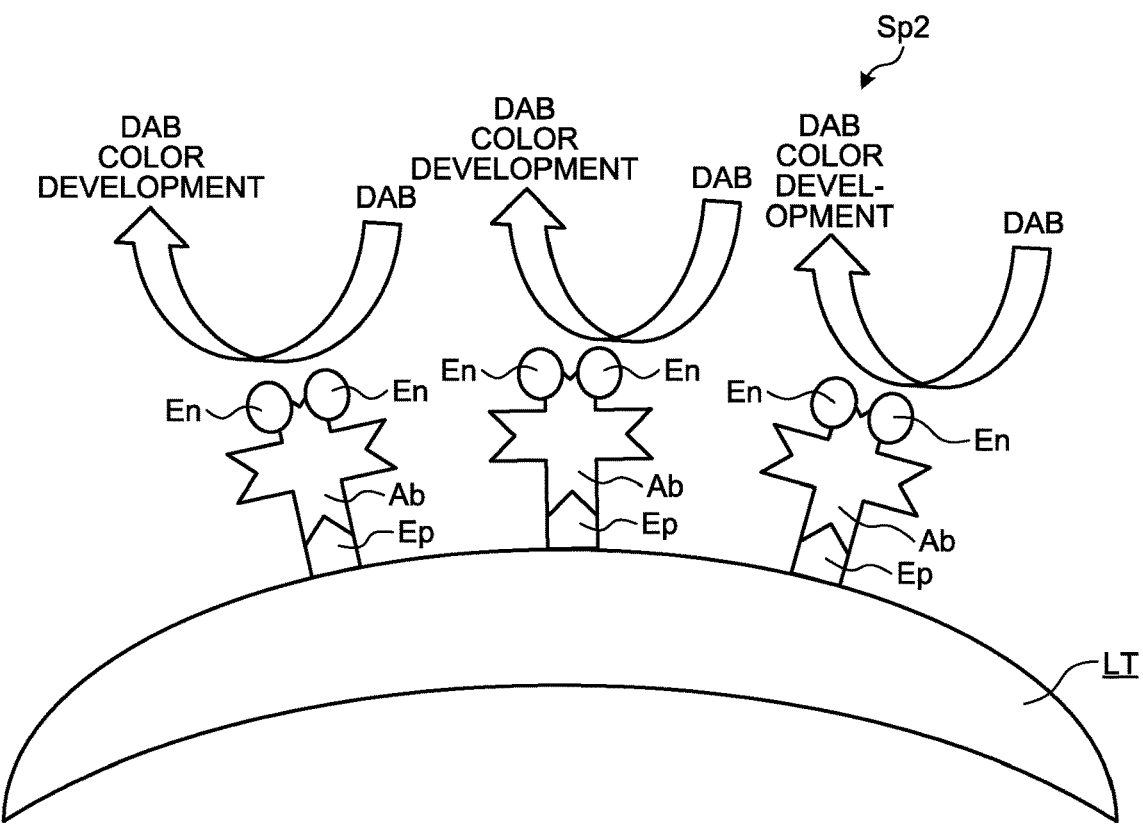
FIG. 12 is a diagram describing a preparation method of a non-specific binding specimen according to the second embodiment.

FIG. 12 is a diagram describing the preparation method of the non-specific binding specimen Sp2 according to the second embodiment.

However, there are many tissues LT containing the endogenous biotin as the endogenous protein. For this reason, in the pathological specimen Sp1, the avidin Ab contained in the avidin-biotin complex ABC may be bound to the endogenous biotin, and thus, the non-specific binding region may be generated in which the DAB reacts with the enzyme (the peroxidase) En contained in the avidin-biotin complex ABC and develops the color. That is, in the pathological specimen Sp1, it is difficult to discriminate whether it is the position of the antigen A0 or the position of the non-specific binding region (a position in which the endogenous protein (the endogenous biotin) exists) from the color development position of the DAB. Therefore, as described below, the non-specific binding specimen Sp2 is prepared in order to separate the position of the antigen A0 from the position of the non-specific binding region.

Specifically, as illustrated in FIG. 12, the operator allows the avidin Ab bound with the enzyme (the peroxidase) En to act on the tissue LT, and binds the avidin Ab to the endogenous biotin that is the endogenous protein Ep. After that, the operator cleans the tissue LT. As a result thereof, the avidin Ab that is not bound to the endogenous biotin that is the endogenous protein Ep is removed from the tissue LT. Then, the operator allows the DAB to act on the tissue LT. Accordingly, the non-specific binding specimen Sp2 that allows the DAB to develop the color by the enzyme (the peroxidase) En bound to the avidin Ab only in the non-specific binding region in which the endogenous biotin that is the endogenous protein Ep exists is prepared.

Even in the case of adopting the preparation method of the pathological specimen Sp1 and the non-specific binding specimen Sp2 as in the second embodiment described above, the same effects as those in the first embodiment described above are obtained.

Modification Example 2-1 of Second Embodiment

Figure 13:
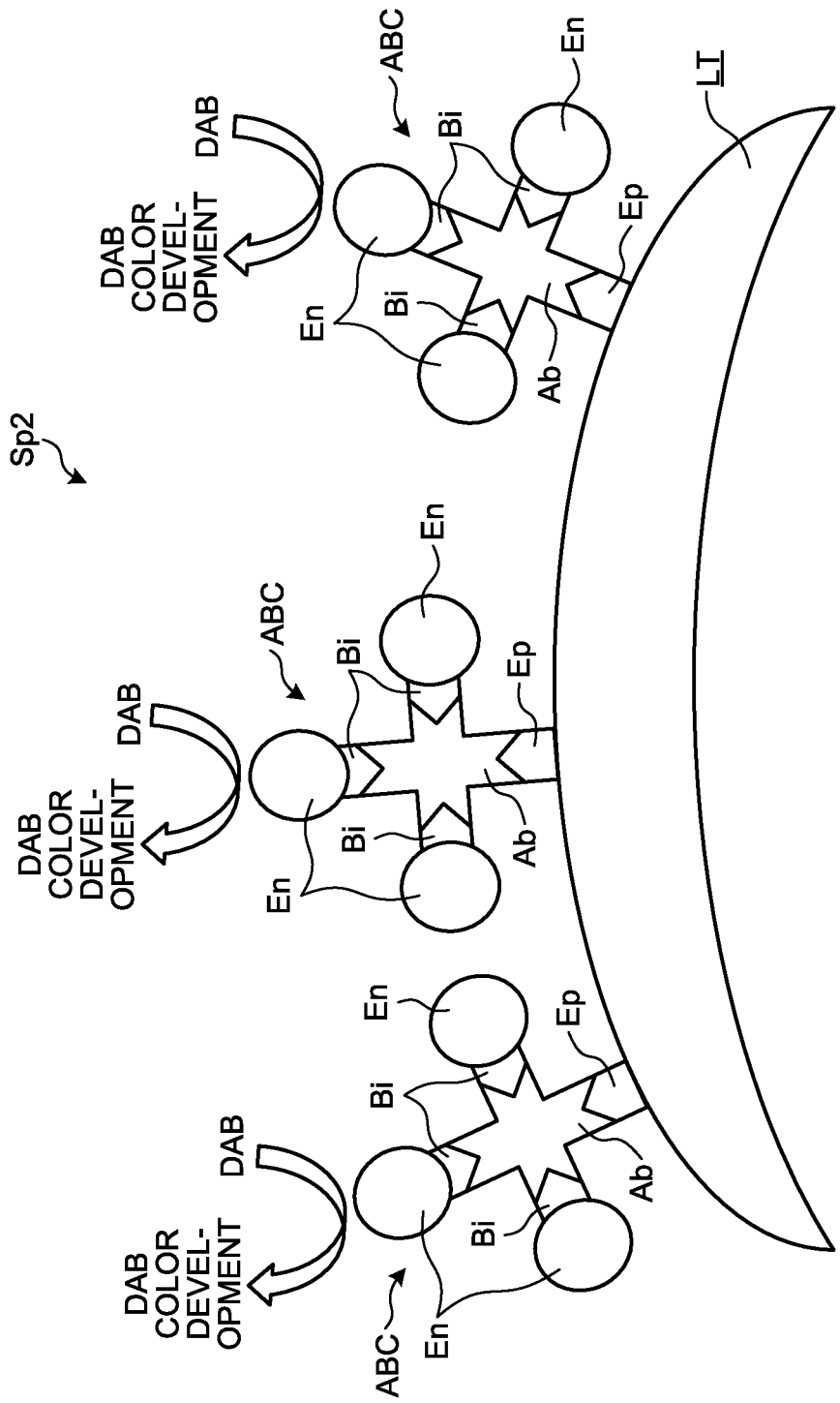
FIG. 13 is a diagram illustrating Modification Example 2-1 of the second embodiment.
Figure 14:
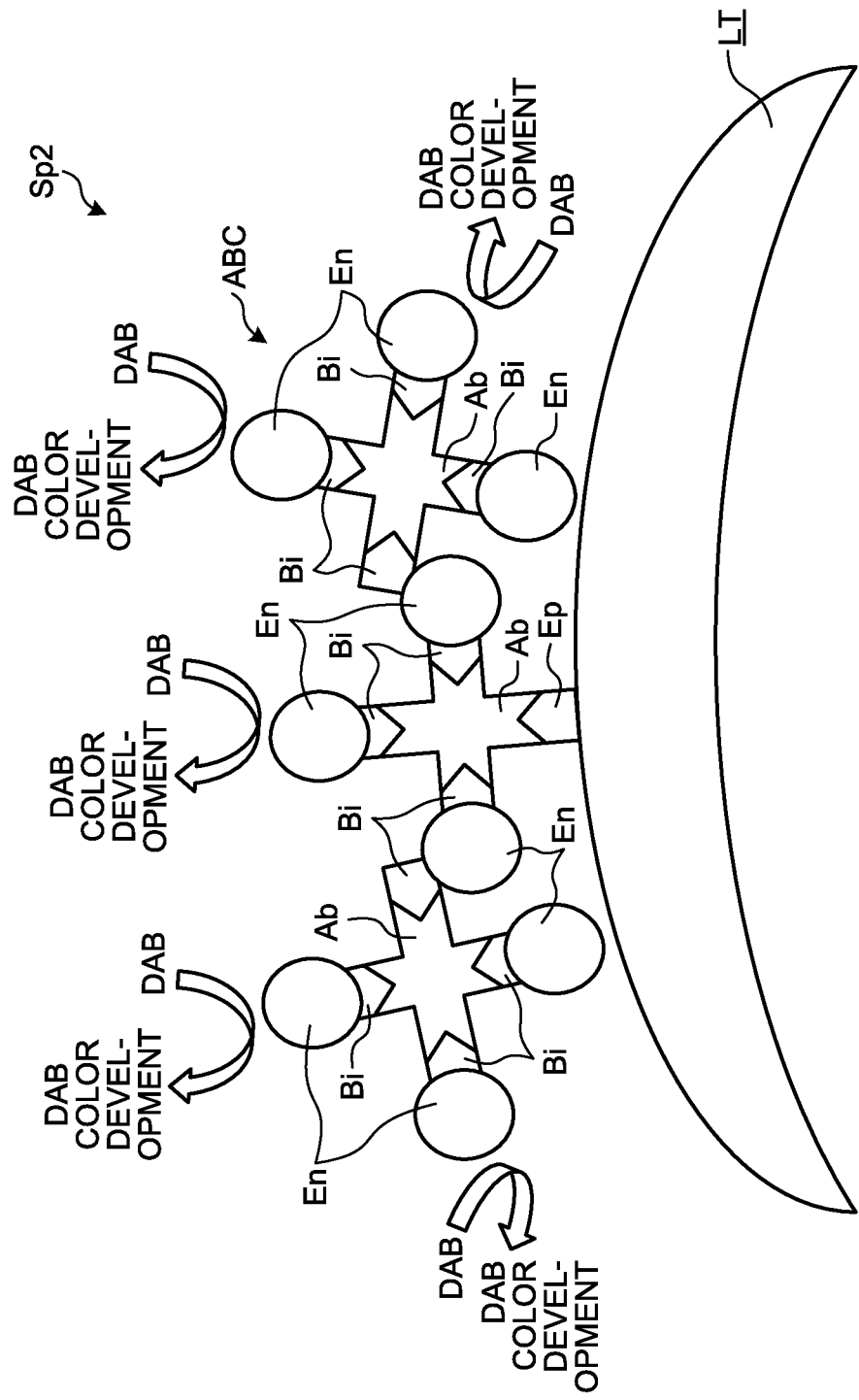
FIG. 14 is a diagram illustrating Modification Example 2-1 of the second embodiment.

FIG. 13 and FIG. 14 are diagrams illustrating Modification Example 2-1 of the second embodiment.

In the second embodiment described above, as illustrated in FIG. 13 or FIG. 14, the non-specific binding specimen Sp2 may be prepared.

Specifically, as illustrated in FIG. 13 or FIG. 14, the operator allows the avidin-biotin complex ABC to act on the tissue LT, and binds the endogenous biotin that is the endogenous protein Ep to the avidin Ab contained in the avidin-biotin complex ABC. After that, the operator cleans the tissue LT. As a result thereof, the avidin-biotin complex ABC (the avidin Ab) that is not bound to the endogenous biotin that is the endogenous protein Ep is removed from the tissue LT. Then, the operator allows the DAB to act on the tissue LT. Accordingly, the non-specific binding specimen Sp2 that allows the DAB to develop the color by the enzyme (the peroxidase) En contained in the avidin-biotin complex ABC only in the non-specific binding region in which the endogenous biotin that is the endogenous protein Ep exists is prepared.

As described above, in a case where the non-specific binding specimen Sp2 is prepared, a large amount of enzyme (peroxidase) En is capable of existing in a position in which the endogenous protein Ep exists, and thus, it is possible to generate the non-specific binding region with a more excellent sensitivity.

Modification Example 2-2 of Second Embodiment

In the second embodiment and Modification Example 2-1 described above, when the pathological specimen Sp1 and the non-specific binding specimen Sp2 are prepared (FIG. 11 to FIG. 14), aminoethyl carbazole or the like may be used instead of the DAB.

In addition, in the second embodiment and Modification Example 2-1 described above, when the pathological specimen Sp1 and the non-specific binding specimen Sp2 are prepared (FIG. 11 to FIG. 14), the alkali phosphatase may be used as the enzyme En instead of the peroxidase, and the fast red or the new fuchsin, the BCIP/NBT, or the like may be used instead of the DAB.

Third Embodiment

Next, a third embodiment will be described.
In the following description, the same reference numerals will be applied to the same configurations and the same steps as those in the first embodiment described above, and the detailed description thereof will be omitted or simplified.

In the third embodiment, only the preparation method of the pathological specimen Sp1 and the non-specific binding specimen Sp2 is different from that in the first embodiment described above.

Hereinafter, the preparation method of the pathological specimen Sp1 and the non-specific binding specimen Sp2 according to the third embodiment will be sequentially described.

Preparation Method of Pathological Specimen

Figure 15:
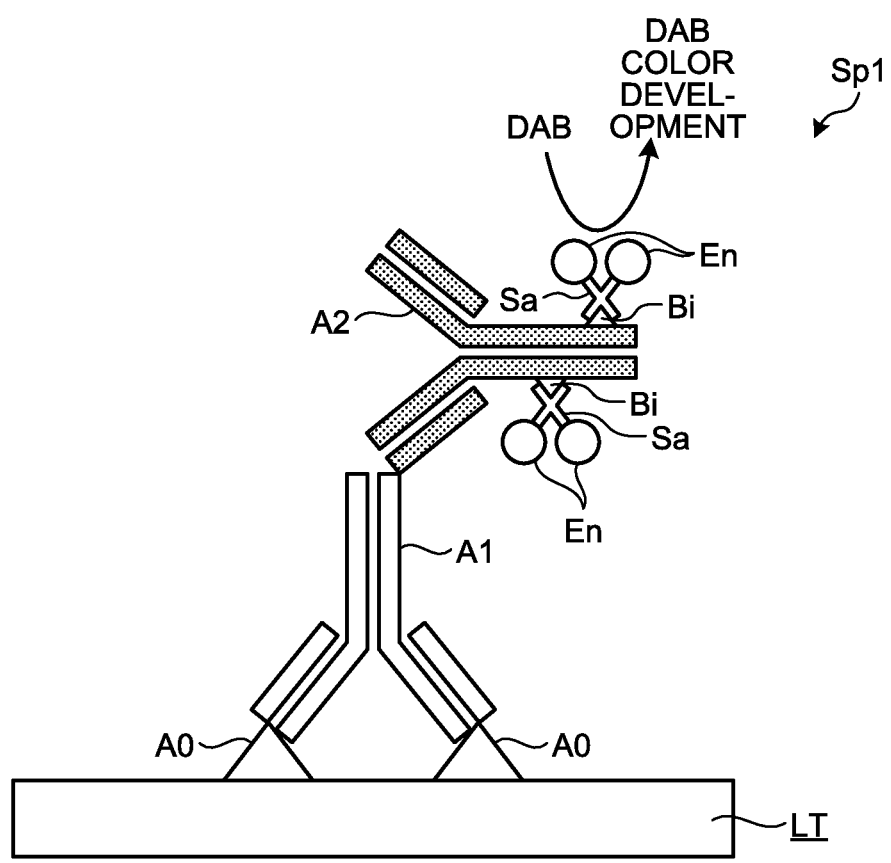
FIG. 15 is a diagram describing a preparation method of a pathological specimen according to a third embodiment.

FIG. 15 is a diagram describing the preparation method of the pathological specimen Sp1 according to the third embodiment.

In the third embodiment, the pathological specimen Sp1 is stained by a staining method illustrated in FIG. 15. Note that, the staining method illustrated in FIG. 15 is a labeled streptavidin biotinylated antibody (LSAB) method that is one of the staining methods for immunostaining.

Specifically, as illustrated in FIG. 15, the operator allows the primary antibody A1 to act on the tissue LT, and binds the primary antibody A1 to the antigen A0 in the tissue LT. After that, the operator cleans the tissue LT. As a result thereof, the primary antibody A1 that is not bound to the antigen A0 is removed from the tissue LT.

Next, the operator allows the biotinylated secondary antibody A2 to act on the tissue LT, and binds the secondary antibody A2 to the primary antibody A1. After that, the operator cleans the tissue LT. As a result thereof, the secondary antibody A2 that is not bound to the primary antibody A1 is removed from the tissue LT.

Next, the operator allows enzyme labeled streptavidin Sa to act on the tissue LT, and binds the enzyme labeled streptavidin Sa to the biotin Bi in the secondary antibody A2. Here, in the third embodiment, the peroxidase is adopted as the enzyme En in the enzyme labeled streptavidin Sa. After that, the operator cleans the tissue LT. As a result thereof, the enzyme labeled streptavidin Sa that is not bound to the secondary antibody A2 (the biotin Bi) is removed from the tissue LT.

Finally, the operator allows the DAB to act on the tissue LT. As a result thereof, the enzyme (the peroxidase) En in the enzyme labeled streptavidin Sa reacts with the DAB, and thus, the DAB develops the color.

According to the processes described above, the pathological specimen Sp1 is prepared.

Preparation Method of Non-Specific Binding Specimen

However, as described in the second embodiment described above, there are many tissues LT containing the endogenous biotin as the endogenous protein. For this reason, in the pathological specimen Sp1, the enzyme labeled streptavidin Sa may be bound to the endogenous biotin, and the non-specific binding region may be generated in which the DAB reacts with the enzyme (the peroxidase) En in the enzyme labeled streptavidin Sa and develops the color. That is, in the pathological specimen Sp1, it is difficult to discriminate whether it is the position of the antigen A0 or the position of the non-specific binding region (a position in which the endogenous protein (the endogenous biotin) exists) from the color development position of the DAB. Therefore, as described below, the non-specific binding specimen Sp2 is prepared in order to separate the position of the antigen A0 from the position of the non-specific binding region.

Specifically, the operator allows the enzyme labeled streptavidin Sa to act on the tissue LT, and binds the enzyme labeled streptavidin Sa to the endogenous biotin that is the endogenous protein Ep. Then, the operator allows the DAB to act on the tissue LT. Accordingly, the non-specific binding specimen Sp2 that allows the DAB to develop the color by the enzyme (the peroxidase) En in the enzyme labeled streptavidin Sa only in the non-specific binding region in which the endogenous biotin that is the endogenous protein Ep exists is prepared.

Even in the case of adopting the preparation method of the pathological specimen Sp1 and the non-specific binding specimen Sp2 as in the third embodiment described above, the same effects as those in the first embodiment described above are obtained.

Modification Example 3-1 of Third Embodiment

In the third embodiment described above, when the pathological specimen Sp1 and the non-specific binding specimen Sp2 are prepared (FIG. 15), the aminoethyl carbazole or the like may be used instead of the DAB.

In addition, in the third embodiment described above, when the pathological specimen Sp1 and the non-specific binding specimen Sp2 are prepared (FIG. 15), the alkali phosphatase may be used as the enzyme En, instead of the peroxidase, and the fast red or the new fuchsin, the BCIP/NBT, or the like may be used instead of the DAB.

Fourth Embodiment

Next, a fourth embodiment will be described.

In the following description, the same reference numerals will be applied to the same configurations and the same steps as those in the first embodiment described above, and the detailed description thereof will be omitted or simplified.

Figure 16:
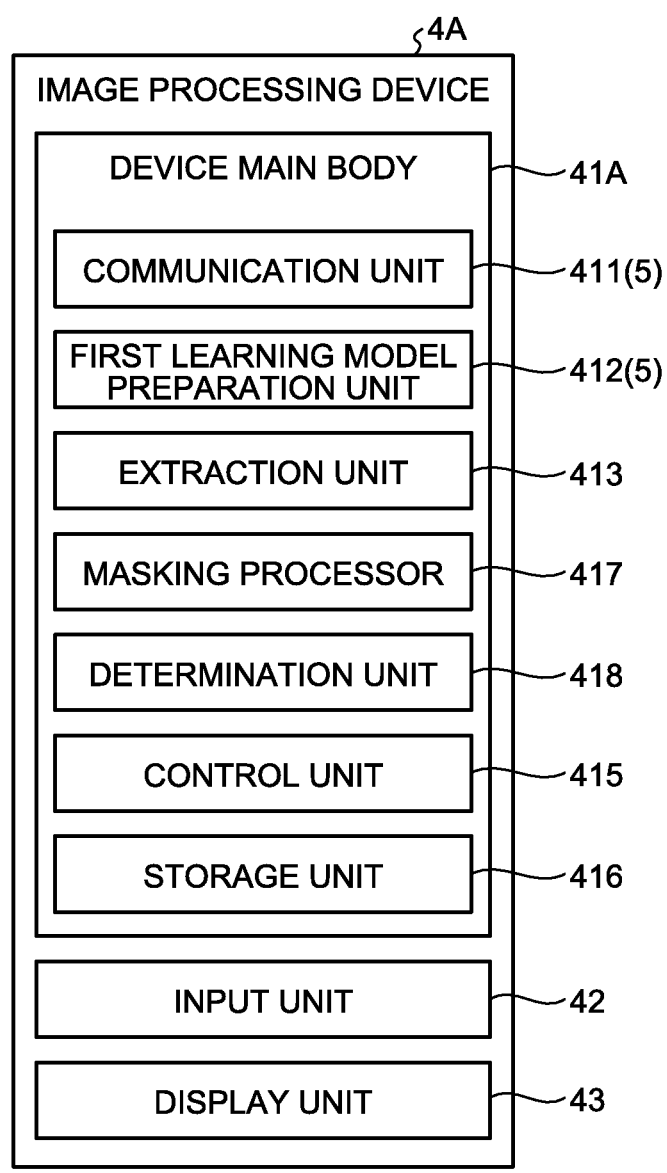
FIG. 16 is a block diagram illustrating an image processing device according to a fourth embodiment.

FIG. 16 is a block diagram illustrating an image processing device 4A according to the fourth embodiment.

In the fourth embodiment, as illustrated in FIG. 16, the image processing device 4A (a device main body 41A) in which the function of the display controller 414 is omitted from the image processing device 4 (the device main body 41) and the functions of a masking processor 417 and a determination unit 418 are added, in the first embodiment described above, is adopted.

Functions of Masking Processor and Determination Unit

The masking processor 417 removes the non-specific binding region that is extracted by the extraction unit 413 from the pathological specimen image that is acquired from the imaging device 2 through the communication unit 411.

The determination unit 418 compares a pixel value for each pixel in the image region that remains without being removed with a predetermined threshold value, on the basis of the pathological specimen image from which the non-specific binding region is removed by the masking processor 417, and thus, determines whether the pathological specimen Sp1 is positive or negative.

Operation of Image Processing Device

Next, the operation of the image processing device 4A described above will be described.

The operation of the image processing device 4A according to the fourth embodiment is different from the operation (the learning model preparation method and the image processing method) of the image processing device 4 described in the first embodiment described above only in the image processing method. For this reason, hereinafter, only the image processing method according to the fourth embodiment will be described.

Figure 17:
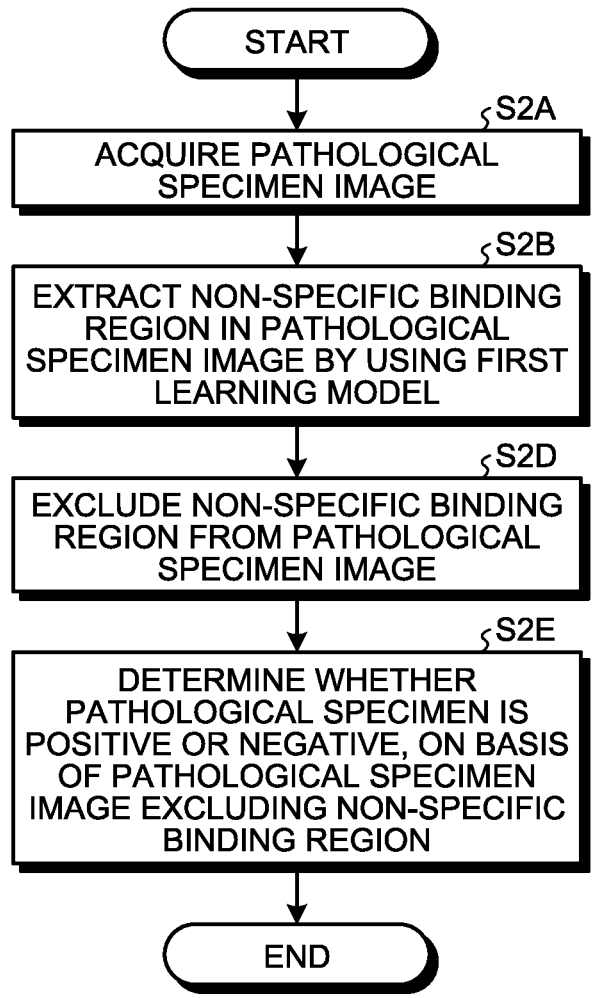
FIG. 17 is a flowchart illustrating an image processing method according to the fourth embodiment.

FIG. 17 is a flowchart illustrating the image processing method according to the fourth embodiment.

As illustrated in FIG. 17, the image processing method according to the fourth embodiment is different from the image processing method (FIG. 9) described in the first embodiment described above in that Step S2C is omitted, and Steps S2D and S2E are added. For this reason, hereinafter, Steps S2D and S2E will be described.

Step S2D (a masking processing step) is executed after Step S2B.

Specifically, in Step S2D, the masking processor 417 removes the non-specific binding region that is extracted in Step S2B from the pathological specimen image that is acquired in Step S2A, under the control of the control unit 415.

After Step S2D, the determination unit 418 compares the pixel value for each of the pixels in the image region that remains without being removed with the predetermined threshold value, on the basis of the pathological specimen image from which the non-specific binding region is removed in Step S2D, and thus, determines whether the pathological specimen Sp1 is positive or negative, under the control of the control unit 415 (Step S2E: a determination step).

According to the fourth embodiment described above, the following effects are obtained in addition to the same effects as those in the first embodiment described above.

The image processing device 4A according to the fourth embodiment acquires the pathological specimen image representing the pathological specimen Sp1 that is the object to be inspected, and extracts the non-specific binding region in the pathological specimen image by using the first learning data. In addition, the image processing device 4A removes the non-specific binding region from the pathological specimen image. Then, the image processing device 4A compares the pixel value for each of the pixels in the image region that remains without being removed with the threshold value, on the basis of the pathological specimen image from which the non-specific binding region is removed, and thus, determines whether the pathological specimen Sp1 is positive or negative.

Therefore, the comparison with the threshold value is not affected by the non-specific binding region, and thus, it is possible to accurately determine whether the pathological specimen Sp1 is positive or negative.

Fifth Embodiment

Next, a fifth embodiment will be described.

In the following description, the same reference numerals will be applied to the same configurations and the same steps as those in the first embodiment described above, and the detailed description thereof will be omitted or simplified.

Figure 18:
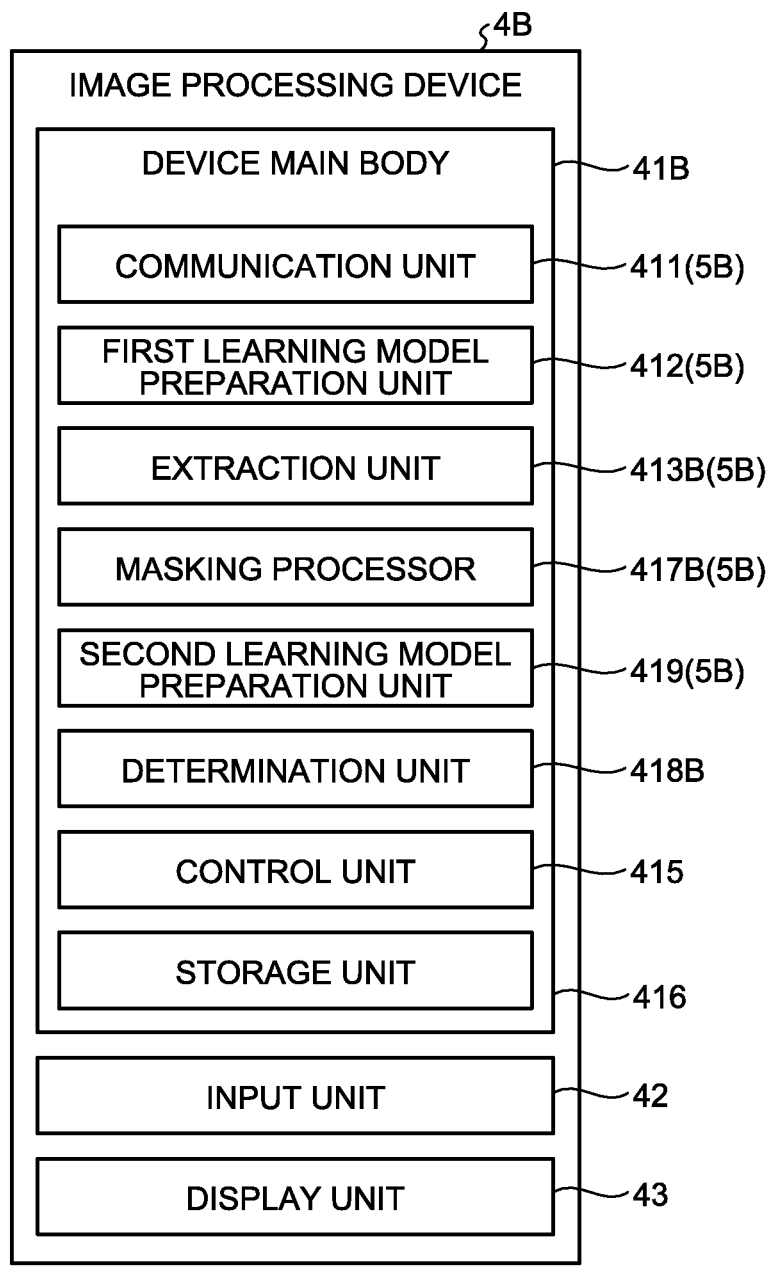
FIG. 18 is a block diagram illustrating an image processing device according to a fifth embodiment.

FIG. 18 is a block diagram illustrating an image processing device 4B according to the fifth embodiment.

In the fifth embodiment, as illustrated in FIG. 18, the image processing device 4B (a device main body 41B) in which the function of the display controller 414 is omitted from the image processing device 4 (the device main body 41) and the function of an extraction unit 413B is adopted instead of the extraction unit 413, and the functions of a masking processor 417B, a determination unit 418B, and a second learning model preparation unit 419 are added, with respect to the first embodiment described above, is adopted.

The database 3 according to the fifth embodiment records a plurality of teacher images described below.

The teacher image is an image that is prepared by acquiring an image representing a tissue specimen that is stained by the same staining method as that of the pathological specimen Sp1 (in the fifth embodiment, the staining method illustrated in FIG. 2A and FIG. 2B) (hereinafter, described as an original image) with the imaging device 2, and by being based on the original image. Specifically, the teacher image is an image in which a positive region and a negative region are respectively labeled (marked) with respect to the original image, for example, by a pathologist.

Functions of Extraction Unit, Masking Processor, Second Learning Model Preparation Unit, and Determination Unit The extraction unit 413B extracts the non-specific binding region in the teacher image that is acquired from the database 3 through the communication unit 411 by using the first learning model stored in the storage unit 416. That is, the communication unit 411 has a function as a second image acquisition unit according to the disclosure.

The masking processor 417B removes the non-specific binding region that is extracted by the extraction unit 413B, from the teacher image that is acquired from the database 3 through the communication unit 411.

The second learning model preparation unit 419 prepares a second learning model by setting the teacher image from which the non-specific binding region is removed by the masking processor 417B to second learning data, and by learning the positive region and the negative region, on the basis of the second learning data. Here, mechanical learning such as linear discrimination or structured learning can be exemplified as the learning. Then, the second learning model preparation unit 419 stores the second learning model in the storage unit 416.

The extraction unit 413B, the masking processor 417B, and the second learning model preparation unit 419 described above configure a learning model preparation device 5B (FIG. 18) according to the disclosure, along with the communication unit 411 and the first learning model preparation unit 412.

The determination unit 418B determines whether the pathological specimen Sp1 is positive or negative from the pathological specimen image that is acquired from the imaging device 2 through the communication unit 411 by using the second learning model stored in the storage unit 416.

Operation of Image Processing Device

Next, in the operation of the image processing device 4B described above, the learning model preparation method and the image processing method will be sequentially described.

Figure 19:
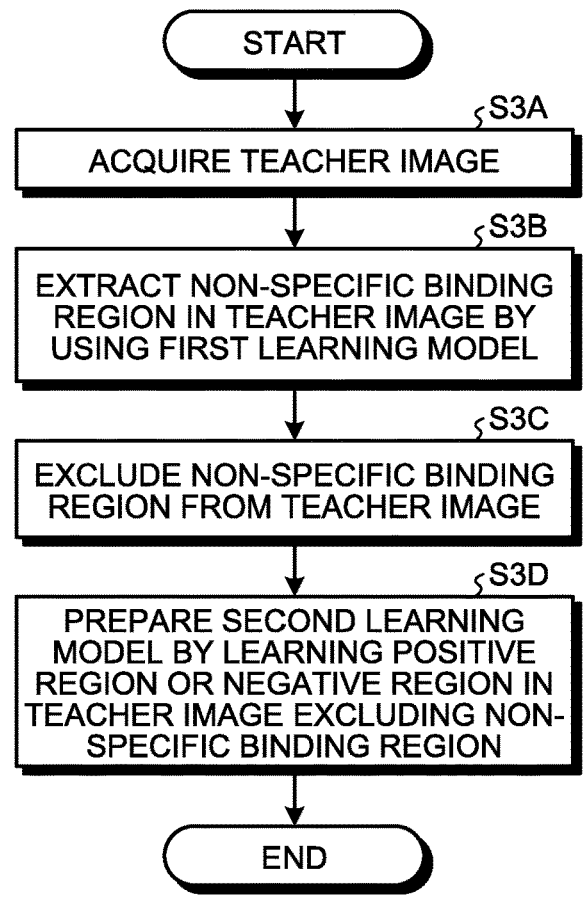
FIG. 19 is a flowchart illustrating a learning model preparation method according to the fifth embodiment.

FIG. 19 is a flowchart illustrating the learning model preparation method according to the fifth embodiment.

Note that, in the storage unit 416, the first learning model that is prepared by the learning model preparation method described in the first embodiment described above is stored in advance.

First, the communication unit 411 acquires the plurality of teacher images recorded in the database 3, under the control of the control unit 415 (Step S3A: a second image acquisition step).

After Step S3A, the extraction unit 413B extracts the non-specific binding region in the teacher image that is acquired in Step S3A by using the first learning model stored in the storage unit 416, under the control of the control unit 415 (Step S3B: an extraction step).

After Step S3B, the masking processor 417B removes the non-specific binding region that is extracted in Step S3B from the teacher image that is acquired in Step S3A, under the control of the control unit 415 (Step S3C: a masking processing step).

After Step S3C, the second learning model preparation unit 419 prepares the second learning model by learning the positive region and the negative region in the plurality of teacher images from which the non-specific binding region is removed in Step S3C, under the control of the control unit 415 (Step S3D: a second learning model preparation step). Then, the second learning model preparation unit 419 stores the second learning model in the storage unit 416.

Figure 20:
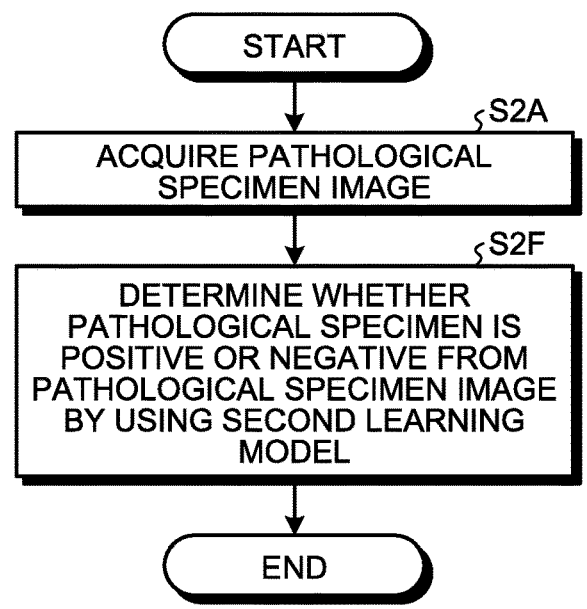
FIG. 20 is a flowchart illustrating an image processing method according to the fifth embodiment.

FIG. 20 is a flowchart illustrating the image processing method according to the fifth embodiment.

As illustrated in FIG. 20, the image processing method according to the fifth embodiment is different from the image processing method (FIG. 9) described in the first embodiment described above in that Steps S2B and S2C are omitted, and Step S2F is added. For this reason, hereinafter, Step S2F will be described.

Step S2F (a determination step) is executed after Step S2A.

Specifically, in Step S2F, the determination unit 418B determines whether the pathological specimen Sp1 is positive or negative from the pathological specimen image that is acquired in Step S2A by using the second learning model stored in the storage unit 416, under the control of the control unit 415.

According to the fifth embodiment described above, the following effects are obtained in addition to the same effects as those in the first embodiment described above.

The image processing device 4B according to the fifth embodiment acquires the teacher image in which the positive region and the negative region of the pathological specimen are marked in advance. In addition, the image processing device 4B extracts the non-specific binding region in the teacher image by using the first learning model, and excludes the non-specific binding region from the teacher image. Further, the image processing device 4B prepares the second learning model by setting the teacher image excluding the non-specific binding region to the second learning data, and by learning the positive region and the negative region, on the basis of the second learning data. Then, the image processing device 4B determines whether the pathological specimen Sp1 is positive or negative from the pathological specimen image representing the pathological specimen Sp1 that is the object to be inspected by using the second learning model.

Therefore, the second learning model excluding the influence of the non-specific binding region is used, and thus, it is possible to accurately determine whether the pathological specimen Sp1 is positive or negative.

Sixth Embodiment

Next, a sixth embodiment will be described.

In the following description, the same reference numerals will be applied to the same configurations and the same steps as those in the first embodiment described above, and the detailed description thereof will be omitted or simplified.

Figure 21:
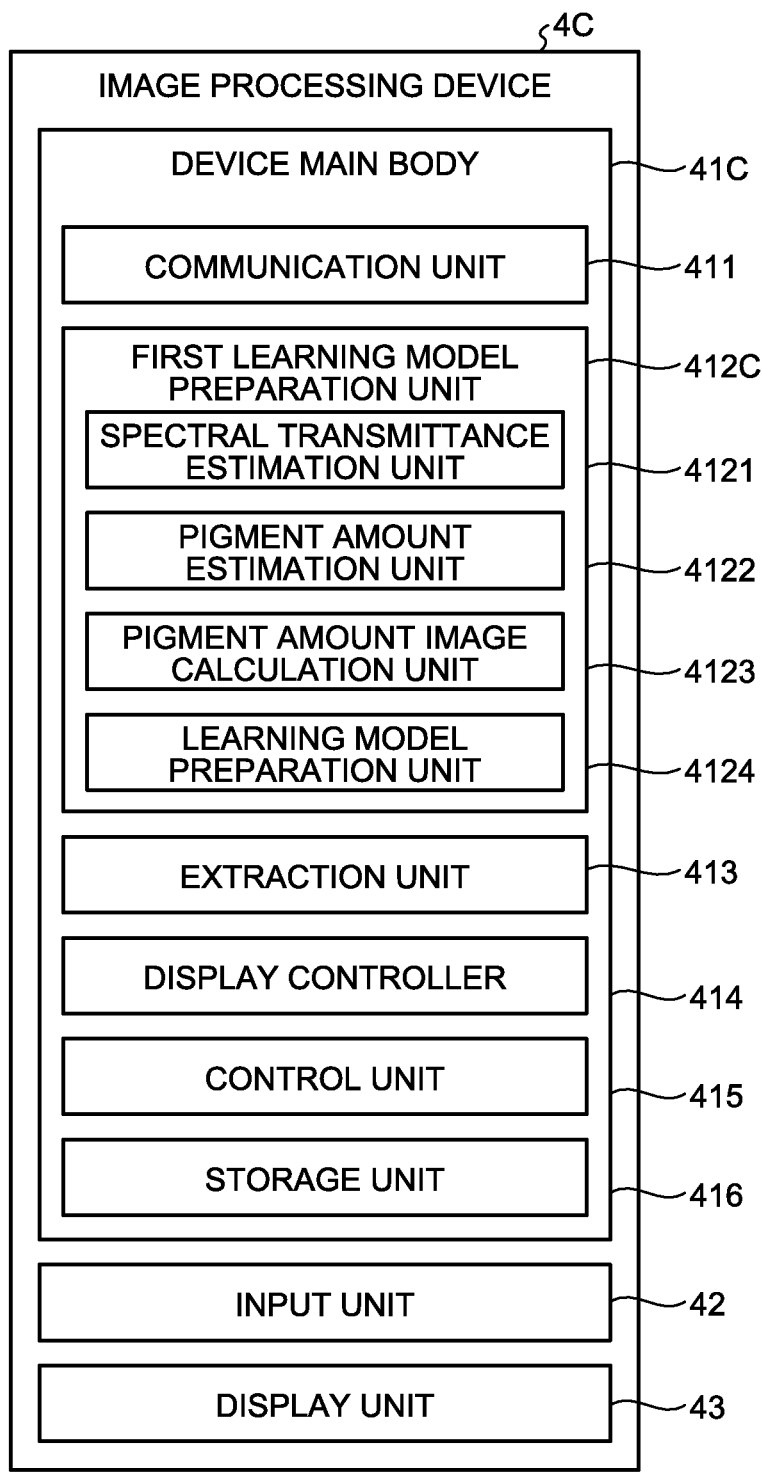
FIG. 21 is a block diagram illustrating an image processing device according to a sixth embodiment.

FIG. 21 is a block diagram illustrating an image processing device 4C according to the sixth embodiment.

In the sixth embodiment, as illustrated in FIG. 21, the image processing device 4C (a device main body 41C) provided with a first learning model preparation unit 412C having a function different from that of the first learning model preparation unit 412 of the image processing device 4, in the first embodiment described above, is adopted.

Hereinafter, an example of an estimation method of a pigment amount in points on the non-specific binding specimen Sp2 from the non-specific binding specimen image (the multiband image) will be described, and then, the function of the first learning model preparation unit 412C will be described.

Example of Estimation Method of Pigment Amount in Points on Non-Specific Binding Specimen Hereinafter, for explanatory convenience, in the non-specific binding specimen Sp2, the DAB is allowed to directly act on the tissue LT as described in the first embodiment described above and the non-specific binding region is visualized by the color development of the DAB (hereinafter, described as a DAB pigment), and hematoxylin is allowed to act on the tissue LT and a negative region (a negative cell) of the tissue LT is visualized by a hematoxylin (H) pigment.

In addition, hereinafter, a case is assumed in which the non-specific binding specimen Sp2 is imaged by a frame sequential method while switching 16 bandpass filters by rotating the filters by the filter wheel. In this case, a multiband image (a non-specific binding specimen image) having pixel values of 16 bands in each point on the non-specific binding specimen Sp2 is obtained. Note that, a pigment is intrinsically three-dimensionally distributed in the non-specific binding specimen Sp2, but is not capable of being directly captured as a three-dimensional image in a general transmissive observation system, and is observed as a two-dimensional image in which the illumination light transmitted through the non-specific binding specimen Sp2 is projected onto the image sensor of the camera. Therefore, here, each of the points indicates a point on the non-specific binding specimen Sp2 corresponding to each projected pixel of the image sensor.

Here, in an arbitrary point (pixel) x of the multiband image (the non-specific binding specimen image) obtained by imaging, a relationship of Expression (1) described below, based on a response system of the camera, is established between a pixel value g(x,b) in a band b and a spectral transmittance t(x,λ) in the corresponding point on the non-specific binding specimen Sp2.

$$g(x,b) = \int_\lambda f(b,\lambda) s(\lambda) e(\lambda) t(x,\lambda) d\lambda + n(b) \quad (1)$$

In Expression (1), λ represents a wavelength, f(b,λ) represents a spectral transmittance of the b-th bandpass filter, s(λ) represents spectral sensitivity properties of the camera, e(λ) represents spectral radiant properties of the illumination, and n(b) represents an observation noise in the band b. b is a serial number for identifying the band, and here, is an integer value satisfying 1≤b≤16. In the actual calculation, Expression (2) described below is used in which Expression (1) is discretized in a wavelength direction.

$$G(x) = FSET(x) + N \quad (2)$$

In Expression (2), in a case where the number of samples in the wavelength direction is D, and the number of bands is B (here, B=16), G(x) is a matrix of B rows and 1 column corresponding to the pixel value g(x,b) in the point x. Similarly, T(x) is a matrix of D rows and 1 column corresponding to t(x,λ), and F is a matrix of B rows and D columns corresponding to f(b,λ). On the other hand, S is a diagonal matrix of D rows and D columns, and an on-diagonal element corresponds to s(λ). Similarly, E is a diagonal matrix of D rows and D columns, and an on-diagonal element corresponds to e(λ). N is a matrix of B rows and 1 column corresponding to n(b). Note that, in Expression (2), expressions relevant to a plurality of bands are aggregated by using the matrix, and thus, a variable b representing the band is not described. In addition, integration relevant to the wavelength λ is replaced with matrix multiplication.

Here, in order to simplify the notation, a matrix H that is defined by Expression (3) described below is introduced. The matrix H is also referred to as a system matrix.

$$H = FSE \quad (3)$$

Accordingly, Expression (2) is replaced with Expression (4) described below.

$$G(x) = HT(x) + N \quad (4)$$

Next, a spectral transmittance in each of the points on the non-specific binding specimen Sp2 is estimated from the multiband image (the non-specific binding specimen image) that is obtained by imaging, by using winner estimation. An estimate value of the spectral transmittance (hereinafter, described as spectral transmittance data) T^(x) can be calculated by Expression (5) described below. Note that, T^ indicates that a symbol "^ (hat)" indicating the estimate value is attached onto T.

$$\hat{T}(x) = WG(x) \quad (5)$$

In Expression (5), W is represented by Expression (6) described below, and is also referred to as a "winner estimation matrix" or an "estimation operator used in winner estimation".

$$W = R_{SS} H^T (H R_{SS} H^T + R_{NN})^{-1} \quad (6)$$

In Expression (6), $R_{SS}$ is a matrix of D rows and D columns, and represents an autocorrelation matrix of the spectral transmittance of the non-specific binding specimen Sp2. In addition, $R_{NN}$ is a matrix of B rows and B columns, and represents an autocorrelation matrix of the noise of the camera that is used in the imaging. Note that, in an arbitrary matrix X, a matrix $X^T$ represents a transposed matrix of the matrix X, and a matrix $X^{-1}$ represents an inverse matrix of the matrix X. The matrices F, S, and E configuring the system matrix H, that is, the spectral transmittance of the bandpass filter, the spectral sensitivity properties of the camera, the spectral radiant properties of the illumination, the matrix $R_{SS}$, and the matrix $R_{NN}$ are acquired in advance.

The spectral transmittance data T^(x) is estimated as described above, and then, the pigment amount in the corresponding point on the non-specific binding specimen Sp2 (hereinafter, described as a specimen point) is estimated on the basis of the spectral transmittance data T^(x). Here, the pigment to be estimated is three types of pigments of an H pigment, a DAB pigment, and a pigment of an erythrocyte body that is not stained (hereinafter, described as an R pigment).

In general, it is found that in a substance that transmits light, a Lambert-Beer law represented by Expression (7) described below is established between an intensity $I_0(\lambda)$ of incident light and an intensity I(λ) of exiting light at each wavelength λ.

$$\frac{I(\lambda)}{I_0(\lambda)} = e^{-k(\lambda)d} \quad (7)$$

In Expression (7), k(λ) represents a unique value of the substance that is set in a manner that depends on the wavelength, and d represents the thickness of the substance. Here, a left-hand side of Expression (7) indicates a spectral transmittance t(λ), and thus, Expression (7) is replaced with Expression (8) described below.

$$t(\lambda) = e^{-k(\lambda)d} \quad (8)$$

In addition, a spectral absorbance $a(\lambda)$ is represented by Expression (9) described below.

$$a(\lambda)=k(\lambda)d \quad (9)$$

Accordingly, Expression (8) is replaced with Expression (10) described below.

$$t(\lambda)=e^{-a(\lambda)} \quad (10)$$

In a case where the non-specific binding specimen Sp2 is stained by three types of pigments of the H pigment, the DAB pigment, and the R pigment, Expression (11) described below is established at each wavelength $\lambda$ by the Lambert-Beer law.

$$\frac{I(\lambda)}{I_0(\lambda)} = e^{-(k_H(\lambda)d_H + k_{DAB}(\lambda)d_{DAB} + k_R(\lambda)d_R)} \quad (11)$$

In Expression (11), $k_H(\lambda)$, $k_{DAB}(\lambda)$, and $k_R(\lambda)$ respectively represent $k(\lambda)$ corresponding to the H pigment, the DAB pigment, and the R pigment, and for example, a pigment spectrum of each of the pigments staining the non-specific binding specimen Sp2 (hereinafter, described as a standard pigment spectrum). In addition, $d_H$, $d_{DAB}$, and $d_R$ represent virtual thicknesses of the H pigment, the DAB pigment, and the R pigment in each specimen point corresponding to each pixel position of the multiband image (the non-specific binding specimen image). Intrinsically, the pigment exists by being dispersed in the non-specific binding specimen Sp2, and thus, the concept of thickness is not accurate, but is an index of a relative pigment amount representing the amount of pigment that exists, compared to a case where the non-specific binding specimen Sp2 is stained by a single pigment. That is, $d_H$, $d_{DAB}$, and $d_R$ respectively represent the pigment amounts of the H pigment, the DAB pigment, and the R pigment. Note that, $k_H(\lambda)$, $k_{DAB}(\lambda)$, and $k_R(\lambda)$ can be easily obtained from the Lambert-Beer law by preparing in advance the non-specific binding specimen Sp2 that is individually stained by each of the H pigment, the DAB pigment, and the R pigment, and by measuring the spectral transmittance thereof with a spectroscope.

Here, in a case where the spectral transmittance in the position x is set to $t(x,\lambda)$, and the spectral absorbance is set to $a(x,\lambda)$, Expression (9) is replaced with Expression (12) described below.

$$a(x,\lambda)=k_H(\lambda)d_H + k_{DAB}(\lambda)d_{DAB} + k_R(\lambda)d_R \quad (12)$$

Then, in a case where an estimate spectral transmittance is set to $\hat{t}(x,\lambda)$ and an estimate spectral absorbance is set to $\hat{a}(x,\lambda)$, at the wavelength $\lambda$ of the spectral transmittance data $\hat{T}(x)$ that is estimated by using Expression (5), Expression (12) is replaced with Expression (13) described below. Note that, $\hat{t}$ indicates that the symbol "^" is attached onto $t$, and $\hat{a}$ indicates that the symbol "^" is attached onto $a$.

$$\hat{a}(x,\lambda)=k_H(\lambda)d_H + k_{DAB}(\lambda)d_{DAB} + k_R(\lambda)d_R \quad (13)$$

In Expression (13), there are three unknown variables of $d_H$, $d_{DAB}$, and $d_R$, and thus, in the case of setting up simultaneous Expression (13) with respect to at least three different wavelengths $\lambda$, it is possible to solve the unknown variables. In order to further increase an accuracy, multiple regression analysis may be performed by setting up simultaneous Expression (13) with respect to four or more different wavelengths $\lambda$. For example, in the case of setting up simultaneous Expression (13) with respect to three wavelengths $\lambda_1$, $\lambda_2$, and $\lambda_3$, matrix notation can be performed as with Expression (14) described below.

$$\begin{pmatrix} \hat{a}(x,\lambda_1) \\ \hat{a}(x,\lambda_2) \\ \hat{a}(x,\lambda_{23}) \end{pmatrix} = \begin{pmatrix} k_H(\lambda_1) & k_{DAB}(\lambda_1) & k_R(\lambda_1) \\ k_H(\lambda_2) & k_{DAB}(\lambda_2) & k_R(\lambda_2) \\ k_H(\lambda_3) & k_{DAB}(\lambda_3) & k_R(\lambda_3) \end{pmatrix} \begin{pmatrix} d_H \\ d_{DAB} \\ d_R \end{pmatrix} \quad (14)$$

Here, Expression (14) is replaced with Expression (15) described below.

$$\hat{A}(x)=Kd(x) \quad (15)$$

In Expression (15), in a case where the number of samples in the wavelength direction is set to D, $\hat{A}(x)$ is a matrix of D rows and 1 column corresponding to $\hat{a}(x,\lambda)$, K is a matrix of D rows and 3 columns corresponding to $k(\lambda)$, and $d(x)$ is a matrix of 3 rows and 1 column corresponding to $d_H$, $d_{DAB}$, and $d_R$ in the point x. Note that, $\hat{A}$ indicates that the symbol "^" is attached onto A.

Then, according to Expression (15), the pigment amounts $d_H$, $d_{DAB}$, and $d_R$ are calculated by using a least-square method. The least-square method is a method for determining $d(x)$ such that the sum of squares of an error in a single regression expression is minimized, and $d(x)$ can be calculated by Expression (16) described below. Note that, in Expression (16) described below, $\hat{d}(x)$ is a pigment amount that is estimated.

$$\hat{d}(x)=(K^T K)^{-1}K^T \hat{A}(x) \quad (16)$$

Function of First Learning Model Preparation Unit

As illustrated in FIG. 21, the first learning model preparation unit 412C includes a spectral transmittance estimation unit 4121, a pigment amount estimation unit 4122, a pigment amount image calculation unit 4123, and a learning model preparation unit 4124.

The spectral transmittance estimation unit 4121, for example, estimates the spectral transmittance of each of the pixels from the non-specific binding specimen image that is acquired from the database 3 through the communication unit 411, by the winner estimation (Expressions (1) to (6)).

The pigment amount estimation unit 4122, for example, estimates the pigment amount of the reagent (the DAB) (the pigment amount of the DAB pigment) for each of the pixels by using the spectral transmittance that is estimated by the spectral transmittance estimation unit 4121, by the Lambert-Beer law (Expressions (7) to (16)).

The pigment amount image calculation unit 4123 calculates a pigment amount image (an image representing the color development state of the reagent (the DAB)) in which the pigment amount of the DAB pigment for each of the pixels that is estimated by the pigment amount estimation unit 4122 is set to each of the pixel values.

The learning model preparation unit 4124 prepares the first learning model by setting a plurality of pigment amount images that are calculated by the pigment amount image calculation unit 4123 to the first learning data, and by learning the non-specific binding region, on the basis of the first learning data. Here, mechanical learning such as linear discrimination or structured learning can be exemplified as the learning. Then, the learning model preparation unit 4124 stores the first learning model in the storage unit 416.

Operation of Image Processing Device

Next, the operation of the image processing device 4C described above will be described.

The operation of the image processing device 4C according to the sixth embodiment is different from the operation (the learning model preparation method and the image processing method) of the image processing device 4 described in the first embodiment described above only in the learning model preparation method. For this reason, hereinafter, only the learning model preparation method according to the sixth embodiment will be described.

FIG. 22 is a flowchart illustrating the learning model preparation method according to the sixth embodiment.

As illustrated in FIG. 22, the learning model preparation method according to the sixth embodiment is different from the learning model preparation method (FIG. 8) described in the first embodiment described above in that Steps S1C to S1F are adopted instead of Step S1B. For this reason, hereinafter, Steps S1C to S1F will be described.

Step S1C is executed after Step S1A.

Specifically, in Step S1C, the spectral transmittance estimation unit 4121 estimates the spectral transmittance of each of the pixels from the non-specific binding specimen image that is acquired in Step S1A, under the control of the control unit 415.

After Step S1C, the pigment amount estimation unit 4122 estimates the pigment amount of the reagent (the DAB) (the pigment amount of the DAB pigment) for each of the pixels by using the spectral transmittance that is estimated in Step S1C, under the control of the control unit 415 (Step S1D: a pigment amount estimation procedure).

After Step S1D, the pigment amount image calculation unit 4123 calculates the pigment amount image in which the pigment amount of the DAB pigment for each of the pixels that is estimated in Step S1D is set to each of the pixel values, under the control of the control unit 415 (Step S1E: a pigment amount image calculation procedure).

Steps S1A and S1C to S1E described above are executed with respect to a plurality of different non-specific binding specimen images. That is, Steps S1A and S1C to S1E are executed with respect to each of the plurality of different non-specific binding specimen images, and thus, the plurality of pigment amount images are calculated.

After Step S1E, the learning model preparation unit 4124 prepares the first learning model by learning the non-specific binding region (the DAB pigment) in the plurality of pigment amount images that are calculated in Step S1E, under the control of the control unit 415 (Step S1F: a learning model preparation procedure).

According to the sixth embodiment described above, the following effects are obtained in addition to the same effects as those in the first embodiment described above.

The image processing device 4C according to the sixth embodiment estimates the pigment amount of the reagent (the DAB) for each of the pixels, on the basis of the non-specific binding specimen image. In addition, the image processing device 4C calculates the pigment amount image representing the color development state of the reagent (the DAB), on the basis of the pigment amount of the reagent (the DAB) for each of the pixels. Then, the image processing device 4C prepares the first learning model by setting the pigment amount image to the first learning data, and by learning the non-specific binding region, on the basis of the first learning data.

That is, the pigment amount image is an image accurately representing the pigment amount of the reagent (the DAB) for each of the pixels, in other words, a non-binding region. For this reason, it is possible to accurately learn the non-specific binding region by setting the pigment amount image to the first learning data. Therefore, it is possible to more accurately determine whether the pathological specimen Sp1 is positive or negative by using the first learning model that is prepared in accordance with the learning.

Other Embodiments

The modes for implementing the disclosure have been described, but the disclosure is not limited to the first embodiment to the sixth embodiment described above.

In the first embodiment to the sixth embodiment described above and Modification Examples 1-1, 1-2, 2-1, 2-2, and 3-1, the learning model preparation devices 5 and 5B are incorporated in the image processing devices 4 and 4A to 4C, but the disclosure is not limited thereto, and the learning model preparation devices 5 and 5B may be configured as devices separated from the image processing devices 4 and 4A to 4C.

The configurations described in the first embodiment to the sixth embodiment described above and Modification Examples 1-1, 1-2, 2-1, 2-2, and 3-1 may be suitably combined. That is, in the fourth embodiment to the sixth embodiment described above, the preparation method described in the second embodiment and the third embodiment, and Modification Examples 1-1, 1-2, 2-1, 2-2, and 3-1 described above may be adopted as the preparation method of the pathological specimen Sp1 or the non-specific binding specimen Sp2. In addition, in the fourth embodiment and the fifth embodiment described above, the first learning model preparation unit 412C described in the sixth embodiment described above may be adopted instead of the first learning model preparation unit 412.

In the fifth embodiment described above, the second learning model is prepared by learning the positive region and the negative region, on the basis of the teacher image excluding the non-specific binding region, but the disclosure is not limited thereto.

For example, the second learning model may be prepared by learning the positive region and the negative region, on the basis of the teacher image not excluding the non-specific binding region. At this time, in Step S2F, the non-specific binding region is excluded from the pathological specimen image by using the first learning model. Then, whether the pathological specimen Sp1 is positive or negative is determined from the pathological specimen image excluding the non-specific binding region by using the second learning model.

In the sixth embodiment described above, the spectral transmittance estimation unit 4121 and the pigment amount estimation unit 4122 respectively estimate the spectral transmittance and the pigment amount for each of the pixels in the non-specific binding specimen image, but the disclosure is not limited thereto, and the spectral transmittance estimation unit 4121 and the pigment amount estimation unit 4122 may respectively estimate the spectral transmittance and the pigment amount for each region (a region including a plurality of pixels) in the non-specific binding specimen image. In addition, the pigment amount estimation unit 4122 estimates the pigment amount by using the spectral transmittance, but the disclosure is not limited thereto, and the pigment amount of the reagent for each of the pixels may be directly estimated from the pixel value of each of the pixels in the non-specific binding specimen image, or may be estimated by using a look-up table or a pigment amount estimation matrix obtained by regression analysis.

According to a learning model preparation method, an image processing method, a learning model preparation device, an image processing device, a learning model preparation program, and an image processing program of the disclosure, an effect is obtained in which whether a pathological specimen is positive or negative can be accurately determined.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A learning model preparation method, comprising:
   acquiring a non-specific binding specimen image representing a non-specific binding specimen that allows a reagent to act on a tissue containing the endogenous protein, the reagent developing a color in a non-specific binding region in which an endogenous protein exists; and
   preparing a first learning model by setting the non-specific binding specimen image to first learning data, and by allowing a learning device to learn the non-specific binding region, based on the first learning data.

2. The learning model preparation method according to claim 1, wherein
   the endogenous protein is endogenous peroxidase, and
   the non-specific binding specimen is a tissue specimen that allows diaminobenzidine to directly act on the tissue and allows the diaminobenzidine to develop a color by the endogenous peroxidase only in the non-specific binding region in which the endogenous peroxidase exists.

3. The learning model preparation method according to claim 1, wherein
   the endogenous protein is endogenous alkali phosphatase, and
   the non-specific binding specimen is a tissue specimen that allows fast red to directly act on the tissue and allows the fast red to develop a color by the endogenous alkali phosphatase only in the non-specific binding region in which the endogenous alkali phosphatase exists.

4. The learning model preparation method according to claim 1, wherein
   the endogenous protein is endogenous biotin, and
   the non-specific binding specimen is a tissue specimen that allows avidin bound with peroxidase to act on the tissue, allows diaminobenzidine to act on the tissue in a state in which the avidin is bound to the endogenous biotin, and allows the diaminobenzidine to develop a color by the peroxidase only in the non-specific binding region in which the endogenous biotin exists.

5. The learning model preparation method according to claim 1, wherein
   the endogenous protein is endogenous biotin, and
   the non-specific binding specimen is a tissue specimen that allows an avidin-biotin complex in which avidin and biotinylated peroxidase are bound to act on the tissue, allows diaminobenzidine to act on the tissue in a state in which the avidin-biotin complex is bound to the endogenous biotin, and allows the diaminobenzidine to develop a color by the peroxidase only in the non-specific binding region in which the endogenous biotin exists.

6. The learning model preparation method according to claim 1, wherein
   the acquiring includes
   estimating a pigment amount of the reagent, based on the non-specific binding specimen image,
   calculating a pigment amount image representing a color development state of the reagent, based on the pigment amount of the reagent, and
   preparing the first learning model by setting the pigment amount image to the first learning data, and by allowing the learning device to learn the non-specific binding region, based on the first learning data.

7. The learning model preparation method according to claim 1, further comprising:
   acquiring a teacher image in which at least one of a positive region and a negative region of a pathological specimen is marked in advance;
   extracting the non-specific binding region in the teacher image by using the first learning model;
   excluding the non-specific binding region from the teacher image; and
   preparing a second learning model by setting the teacher image excluding the non-specific binding region to second learning data, and by allowing the learning device to learn at least one of the positive region and the negative region, based on the second learning data.

8. An image processing method, comprising:
   acquiring a pathological specimen image representing a pathological specimen that is an object to be inspected;
   extracting the non-specific binding region in the pathological specimen image by using the first learning data that is prepared by the learning model preparation method according to claim 1; and
   displaying the non-specific binding region in the pathological specimen image on a display to be identifiable from other regions in the pathological specimen image.

9. An image processing method, comprising:
   acquiring a pathological specimen image representing a pathological specimen that is an object to be inspected;
   extracting the non-specific binding region in the pathological specimen image by using the first learning model that is prepared by the learning model preparation method according to claim 1;
   excluding the non-specific binding region from the pathological specimen image; and
   determining whether the pathological specimen is positive or negative, based on the pathological specimen image excluding the non-specific binding region.

10. An image processing method, comprising:
    acquiring a pathological specimen image representing a pathological specimen that is an object to be inspected; and
    determining whether the pathological specimen is positive or negative from the pathological specimen image by using the second learning model that is prepared by the learning model preparation method according to claim 7.

11. A learning model preparation device, comprising:
    a first image acquisition circuit configured to acquire a non-specific binding specimen image representing a non-specific binding specimen that allows a reagent to act on a tissue containing the endogenous protein, the reagent developing a color in a non-specific binding region in which an endogenous protein exists; and
    a first learning model preparation circuit configured to prepare a first learning model by setting the non-specific binding specimen image to first learning data, and by learning the non-specific binding region.

12. The learning model preparation device according to claim 11, further comprising:
- a second image acquisition circuit configured to acquire a teacher image in which at least one of a positive region and a negative region of a pathological specimen is marked in advance;
- an extraction circuit configured to extract the non-specific binding region in the teacher image by using the first learning model;
- a masking process circuit configured to exclude the non-specific binding region from the teacher image; and
- a second learning model preparation circuit configured to prepare a second learning model by setting the teacher image excluding the non-specific binding region to second learning data, and by learning at least one of the positive region and the negative region, based on the second learning data.

13. An image processing device, comprising:
- a third image acquisition circuit configured to acquire a pathological specimen image representing a pathological specimen that is an object to be inspected;
- an extraction circuit configured to extract the non-specific binding region in the pathological specimen image by using the first learning data that is prepared by the learning model preparation device according to claim 11; and
- a display controller configured to display the non-specific binding region in the pathological specimen image on a display to be identifiable from other regions in the pathological specimen image.

14. An image processing device, comprising:
- a third image acquisition circuit configured to acquire a pathological specimen image representing a pathological specimen that is an object to be inspected;
- an extraction circuit configured to extract the non-specific binding region in the pathological specimen image by using the first learning model that is prepared by the learning model preparation device according to claim 11;
- a masking process circuit configured to exclude the non-specific binding region from the pathological specimen image; and
- a determination circuit configured to determine whether the pathological specimen is positive or negative, based on the pathological specimen image excluding the non-specific binding region.

15. An image processing device, comprising:
- a third image acquisition circuit configured to acquire a pathological specimen image representing a pathological specimen that is an object to be inspected; and
- a determination circuit configured to determine whether the pathological specimen is positive or negative from the pathological specimen image by using the second learning model that is prepared by the learning model preparation device according to claim 12.

16. A non-transitory computer-readable recording medium with an executable program stored thereon, the program being a learning model preparation program allowing a computer to execute the learning model preparation method according to claim 1.

17. A non-transitory computer-readable recording medium with an executable program stored thereon, the program being an image processing program allowing a computer to execute the image processing method according to claim 8.

* * * * *